(12) United States Patent
Piper

(10) Patent No.: US 7,636,636 B2
(45) Date of Patent: Dec. 22, 2009

(54) IMAGING MICROARRAYS

(75) Inventor: James R. Piper, Aberlady (GB)

(73) Assignee: Abbott Laboratories, Des Plaines, IL (US)

( * ) Notice: Subject to any disclaimer, the term of this patent is extended or adjusted under 35 U.S.C. 154(b) by 170 days.

(21) Appl. No.: 10/269,723

(22) Filed: Oct. 11, 2002

(65) Prior Publication Data

US 2003/0124589 A1 Jul. 3, 2003

Related U.S. Application Data

(60) Provisional application No. 60/328,760, filed on Oct. 12, 2001.

(51) Int. Cl.
*G01N 33/48* (2006.01)

(52) U.S. Cl. .............................. 702/19; 700/266; 703/2

(58) Field of Classification Search .................. 702/19, 702/22
See application file for complete search history.

(56) References Cited

U.S. PATENT DOCUMENTS

| | | | |
|---|---|---|---|
| 4,926,251 A | 5/1990 | Sekizawa et al. | |
| 5,127,063 A | 6/1992 | Nishiya et al. | |
| 5,155,558 A | 10/1992 | Tannenbaum et al. | |
| 5,291,563 A | 3/1994 | Maeda | |
| 5,638,460 A | 6/1997 | Nishimori et al. | |
| 5,663,319 A | 9/1997 | Bittner et al. | |
| 5,756,696 A | 5/1998 | Gray et al. | |
| 5,776,688 A | 7/1998 | Bittner et al. | |
| 5,804,384 A | 9/1998 | Muller et al. | |
| 5,824,478 A | 10/1998 | Muller | |
| 6,140,653 A | 10/2000 | Che | |
| 6,165,714 A | 12/2000 | Lane et al. | |
| 6,221,592 B1 | 4/2001 | Schwartz et al. | |
| 6,251,601 B1 | 6/2001 | Bao et al. | |
| 2002/0097898 A1* | 7/2002 | Brown et al. | ................ 382/128 |

OTHER PUBLICATIONS

Basarsky, T. et al. Overview of a microarray scanner: design essentials for an integrated acquisition and analysis platform, Schena M. (ed.) Microarray Biochip Technology, BioTechniques Books, Natick MA pp. 265-284 (2000).

Chen, Y. et al. Ratio-based decisions and the quantitative analysis of cDNA microarray images. J. Biomedical Optics 2:364-374 (1997).

(Continued)

*Primary Examiner*—Carolyn Smith
(74) *Attorney, Agent, or Firm*—Quine Intellectual Property Law Group; Stephen J. LeBlanc

(57) ABSTRACT

A method of obtaining a corrected image of a microarray includes acquiring an image of a microarray including a target spot, and processing the image to correct for background noise and chip misalignment. The method also includes analyzing the image to identify a target patch, edit debris, and correct for ratio bias; and detecting single copy number variation in the target spot using an objective statistical analysis that includes a t-value statistical analysis. The method provides statistically robust computational processes for accurately detecting genomic variation at the single copy level.

30 Claims, 11 Drawing Sheets

OTHER PUBLICATIONS

Deyholos MK, et al. High density microarrays for gene expression analysis. Cytometry 43:229-238 (2001).

DuManoir, S. et al. "Quantitative analysis of comparative genomic hybridization." Cytometry 19:27-41 (1995).

Eisen, Michael "ScanAlyze User Manual" Copyright 1998-9 Stanford University pp. 1-27.

Heiskanen MA, et al., "Detection of gene amplification by genomic hybridization to cDNA microarrays." Cancer Research 60:799-802 (2000).

Jain AN, et al., Quantitative analysis of chromosomal CGH in human breast tumors associates copy number abnormalities with p53 status and patient survival. PNAS 98:7952-7957 (2001).

Moore, et al. "A t-Statistic for Objective Interpretation of CGH Profiles," Cytometry 28:183-190 (1997), published by Wiley-Liss, Inc.

Pinkel, D., et al, "High resolution analysis of DNA copy number variation using comparative genomic hybridization to microarrays." Nature Genetics, 20:207-211 (Oct. 1998).

Piper, J. et al. "Computer image analysis of comparative genomic hybridization." Cytometry 19:10-26 (1995).

Pollack, J.R., et al. "Genome-wide analysis of DNA copy-number changes using cDNA microarrays." Nature Genetics 23:41-46. (Sep. 1999).

Solinas-Toldo S. et al., Matrix-based comparative genomic hybridization: biochips to screen for genomic imbalances. Genes, Chromosomes & Cancer 20:399-407 (1997).

Zhou X-Y, et al., "Information processing issues and solutions associated with microarray technology." Schena M. (ed.) Microarray Biochip Technology, BioTechniques Books, Natick MA, pp. 167-200 (2000).

GenoSensor Reader System User Guide, Copyright 1999-2001 Vysis Inc. 117 pages total.

GenoSensorV1.0 UserGuide.30-605020 Rev. A 799, Aug. 1999.

GenoSensorV1.0.2 UserGuide.30-605020 Rev. B 500 Jun. 5, 2000.

* cited by examiner

100

Microarray detection process

222

Ratio bias correction

300

302

304

306

--False Positives Table A--

| Threshold | Observed | Predicted |
|---|---|---|
| p<0.01 | 9 | 18 |
| p<0.02 | 35 | 36 |
| p<0.05 | 126 | 90 |

IMAGING MICROARRAYS

CROSS REFERENCE TO RELATED APPLICATIONS

This application claims priority from U.S. Provisional Patent Application No. 60/328,760, filed Oct. 12, 2001. The prior application is incorporated herein by reference in its entirety.

TECHNICAL FIELD

This invention relates to imaging microarrays.

BACKGROUND

Imaging microarray technology is a powerful tool for genetic research in constitutional and cancer genetics.

Typically, a microarray experiment involves hybridizing labeled sample DNA to a chip yielding values for between hundreds and tens of thousands of genes simultaneously. Such an experiment includes the acquisition and analysis of large datasets. Dataset processing includes the preparation of genomic material, microarray fabrication, microarray scanning, image processing, and microarray image analysis. During the image analysis phase, spot quantitation for the stored microarray image of both the test and reference samples is critical for understanding the nature of genomic variations in the test sample.

SUMMARY

According to one aspect of the invention, a method includes acquiring an image of a genomic microarray including a target spot; processing the image to correct for background noise and chip misalignment; analyzing the image to identify a target patch, edit debris, and correct for ratio bias; and, detecting single copy number variation in the target spot using an objective statistical analysis that includes a t-value statistical analysis. In some embodiments, the target spot is Deoxyribonucleic Acid (DNA). One or more of the following features may also be included.

The method can further include preparing a genomic material prior to acquiring the image and generating a microarray of the genomic material on a solid substrate. Preparing the genomic material also includes isolating the genomic material by a DNA extraction process followed by nick translation labeling and polymerase chain reaction (PCR) labeling.

As another feature, the method includes the genomic material having a range between 50-200 kilo base pairs (kbp).

In certain embodiments, the genomic microarray provides a test genomic material marked with green receptors having a first wavelength and a reference genomic material marked with red receptors having a second wavelength. Both test and reference genomic materials form the DNA spot by a hybridization process. The hybridization process is a comparative genomic hybridization (CGH) process.

As another feature, the method additionally includes measuring a fluorescent signal intensity of the target spot from the test genomic material and the reference genomic material. The fluorescent signal intensity of the first wavelength is proportional to a copy number of the test genomic material, and the fluorescent signal intensity of the second wavelength is proportional to a copy number of the reference genomic material.

Further, subsequent to acquiring the image of the genomic microarray and prior to correcting the background noise, processing the image includes automatically detecting misalignment of the genomic microarray and correcting its rotation.

As yet another feature, correcting the rotation of the genomic microarray includes applying a bicubic interpolation computation for pixel values of the image.

The method also includes correcting of the background noise by computing the acquired image; computing a minimum image based on the computed acquired image; computing a maximum image based on the computed minimum image; subtracting a background image from the computed acquired image to obtain a resulting image; and, optimizing the correction of the background noise by identifying a background peak of the resulting image and subtracting the resulting image to obtain a mean value of zero for a corrected image.

The method also includes correcting the background noise where the corrected image includes pixels having signed values. Further, the method also includes identifying a DNA patch which includes obtaining an image of a theoretical set of patches; and, cross-correlating the image of the theoretical set of patches to a counterstained image.

The method also includes following the identifying of a target patch, e.g., a DNA patch, computing a threshold by analyzing a pixel intensity of the counterstained image to determine an initial segmentation of the target spot; and, performing a process for spot shape analysis and spot segmentation.

Further, the method includes performing a spot identification analysis; and performing an artifact spot exclusion process wherein an artifact spot is automatically excluded. Moreover, the editing of debris includes automatically removing a spot debris by recognizing and excluding spot pixels within the target spot having outlying intensity relative to a majority of the spot pixels.

The editing of debris includes transforming test and reference intensities to polar coordinates having as a first coordinate the overall intensity of spot signals and having as a second coordinate the ratio; applying a standard statistical test for outliers to the first and second coordinates; and, analyzing the shape of excluded spot pixels.

In addition, the method includes computing a ratio based on a test and a reference fluorescence signal intensity value associated with the target spot. The correcting of ratio bias includes measuring, for example, a raw ratio representing a ratio of total green fluorescence intensity from the test fluorescence signal intensity value and a total red fluorescence intensity from the reference fluorescence signal intensity value. The method further includes normalizing the raw ratio by mathematical computation.

The correcting the ratio bias includes determining whether a data relating to the image is known or unknown; if the data is known, applying a first ratio bias equation, $R=r^{-B}$, where R is the ratio, and r the reference intensity; and, if the data is unknown, applying a second ratio bias equation, $R_{corrected}=R_{original}/R_{predicted}$, where $R_{corrected}$ is a corrected ratio, $R_{original}$ is an original ratio, and $R_{predicted}$ is a predicted ratio.

The method also includes the objective statistical analysis having a t-value statistical analysis. The t-value statistical analysis includes computing a ratio value using a test:reference data and a test:test data; computing a variance value for the test:reference data and the test:test data; applying an adjusted t-statistical test derived from the ratio and variance values; and, applying a final t-value equation for detecting single copy number variation.

The adjusted t-statistical test includes an equation, $$t(k) = \frac{(\bar{x}_T(k) - \bar{x}_R(k))\sqrt{n_T + n_R - 2}}{\sqrt{\left(\frac{\sigma_T^2(k)}{n_T} + \frac{\sigma_R^2(k)}{n_R}\right)\left(\frac{n_T s_T^2(k)}{\sigma_T^2(k)} + \frac{n_R s_R^2(k)}{\sigma_R^2(k)}\right)}},$$

where $\bar{x}_T(k)$ refers to a test:reference spot mean at a target position k; $n_T$ represents a number of the test:reference spot means; $\sigma_T^2(k)$ is a theoretical variance of the test:reference spot means; $s_T^2(k)$ is a sample variance of the test:reference spot means; $\bar{x}_R(k)$ is a mean of a reference:reference spot means; $n_R$ is a number of the reference:reference spot means; $\sigma_R^2(k)$ is a theoretical variance of the reference:reference spot means; and $s_R^2(k)$ is a sample variance of the reference:reference spot means.

The final t-value equation is represented by $$t(k) = \frac{(\bar{x}_T(k) - \bar{x}_R(k))\sqrt{n_T + n_R - 2}}{\sqrt{\left(\frac{\theta}{n_T} + \frac{1}{n_R}\right)\left(\frac{n_T s_T^2(k)}{\theta} + \frac{n_R s_R^2(k)}{1}\right)}},$$

where the equation provides a final t(k) value including a p-value for a difference between a measured mean ratio and a calibration data mean.

Further, the method includes an objective statistical analysis including a target-modal statistical analysis. The target-modal statistical analysis includes plotting a plausibly model distribution data; determining if the distribution is significantly normal and normalize the distribution data if the distribution is not significantly normal; computing an estimated target mean and a lower 95% value for a confidence limit interval; and reducing the confidence limit interval by a median confidence internal over the spots and calculating a confidence estimate for each spot.

The method includes estimating a relative copy number of a genomic sequence from the target spot using the target-modal statistical analysis.

According to another aspect of the invention, a computer program product residing on a computer readable medium causes the processor to acquire an image of a genomic microarray including a target spot; process the image for correcting of a background noise and chip misalignment; analyze the image for identifying a DNA patch, editing of debris, and correcting a ratio bias. The computer program product also causes the processor to detect of single copy number variation in the target spot using an objective statistical analysis.

One or more of the following features may also be included.

The computer program product further causes the processor to measure a fluorescent signal intensity of the target spot, e.g., DNA, from the test genomic material and the reference genomic material, where the fluorescent signal intensity of the first wavelength is proportional to a copy number of the test genomic material and the fluorescent signal intensity of the second wavelength is proportional to a copy number of the reference genomic material.

Subsequent to causing the processor to acquire the image of the genomic microarray and prior to causing the processor to process the image for correcting the background noise, the computer program product further causes the processor to process the image further includes automatically causing the processor to detect misalignment of the genomic microarray and correct rotation of the genomic microarray. The genomic material includes a range between 50 kbp and 200 kbp.

The genomic microarray includes a test genomic material marked with green receptors having a first wavelength and a reference genomic material marked with red receptors having a second wavelength, both test and reference genomic materials forming the target spot by a hybridization process.

Further, causing the processor to correct rotation of the genomic microarray includes causing the processor to apply a bicubic interpolation computation for pixel values of the image.

The computer program product further causes the processor to compute a ratio based on a test and a reference fluorescence signal intensity value associated with the target spot.

As another feature, the correcting of the ratio bias includes measuring a raw ratio representing a ratio of total green fluorescence intensity from the test fluorescence signal intensity value and a total red fluorescence intensity from the reference fluorescence signal intensity value.

As yet another feature, the computer program product further causes the processor to normalize the raw ratio by mathematical computation.

In certain embodiments, the correcting of the ratio bias includes determining whether a data relating to the image is known or unknown. If the data is known, a first ratio bias equation, $R=r^{-\beta}$ is applied, where R is the ratio, and r the reference intensity. If the data is unknown, a second ratio bias equation, $R_{corrected} = R_{original}/R_{predicted}$ is applied, where $R_{corrected}$ is a corrected ratio, $R_{original}$ is an original ratio, and $R_{predicted}$ is a predicted ratio.

The objective statistical analysis of the computer program product, in certain embodiments, includes a t-value statistical analysis. The t-value statistical analysis includes computing a ratio value using a test:reference data and a test:test data; computing a variance value for the test:reference data and the test:test data; applying an adjusted t-statistical test derived from the ratio and variance values; and, applying a final t-value equation for detecting single copy number variation.

The adjusted t-statistical test includes an equation, $$t(k) = \frac{(\bar{x}_T(k) - \bar{x}_R(k))\sqrt{n_T + n_R - 2}}{\sqrt{\left(\frac{\sigma_T^2(k)}{n_T} + \frac{\sigma_R^2(k)}{n_R}\right)\left(\frac{n_T s_T^2(k)}{\sigma_T^2(k)} + \frac{n_R s_R^2(k)}{\sigma_R^2(k)}\right)}},$$

where $\bar{x}_T(k)$ refers to a test:reference spot mean at a target position k; $n_T$ represents a number of the test:reference spot means; $\sigma_T^2(k)$ is a theoretical variance of the test:reference spot means; $s_T^2(k)$ is a sample variance of the test:reference spot means; $\bar{x}_R(k)$ is a mean of a reference:reference spot means; $n_R$ is a number of the reference:reference spot means; $\sigma_R^2(k)$ is a theoretical variance of the reference:reference spot means; and $s_R^2(k)$ is a sample variance of the reference:reference spot means.

The final t-value equation is $$t(k) = \frac{(\bar{x}_T(k) - \bar{x}_R(k))\sqrt{n_T + n_R - 2}}{\sqrt{\left(\frac{\theta}{n_T} + \frac{1}{n_R}\right)\left(\frac{n_T s_T^2(k)}{\theta} + \frac{n_R s_R^2(k)}{1}\right)}},$$

where the equation provides a final t(k) value.

As another aspect, the objective statistical analysis includes a target-modal statistical analysis. The target-modal statistical analysis includes plotting a plausibly model distribution data; determining if the distribution is significantly normal and normalize the distribution data if the distribution is not significantly normal. The target-modal statistical analysis also includes computing an estimated target mean and a lower 95% value for a confidence limit interval; and, reducing the confidence limit interval by a median confidence internal over the spots and calculating a confidence estimate for each spot.

According to another aspect of the invention, a processor and a memory are provided which are configured to acquire an image of a genomic microarray including a target spot; to process the image for correcting of a background noise and chip misalignment; to analyze the image for identifying a DNA patch, editing of debris, and correcting a ratio bias; and, to detect single copy number variation in the target spot using an objective statistical analysis.

According to yet another aspect of the invention, a system includes means for acquiring an image of a genomic microarray including a target spot; means for processing the image for correcting of a background noise and chip misalignment; means for analyzing the image for identifying a DNA patch, editing of debris, and correcting a ratio bias; and, means for detecting single copy number variation in the target spot using an objective statistical analysis.

Embodiments may have one or more of the following advantages.

The methods and systems offer the ability to study complete genomes at the molecular level and in a largely automated fashion making DNA microarray technology a powerful analytical tool.

The methods further provide statistically robust computational processes capable of accurately detecting genomic variation at the single copy level.

Manual adjustment and human intervention qualifies as a bottleneck in the microarray analysis process. Consequently, the methods provide reduce human intervention, offering an automated and objective solution for microarray quantitation.

The methods further provide speed of processing and analysis, allowing image acquisition and analysis in an accurate manner without unnecessary delays caused by non-automated processes. A microarray computational environment provides a user with options for concatenating a number of tasks thus allowing the user to analyze images as they are acquired in the acquisition process.

An integrated microarray image acquisition and analysis process also provides a high level of sensitivity giving precise measurements at the single copy level.

A user is not required to wade through complicated dialog boxes to complete simple tasks such as generating a ratio image, making the method efficient and user-friendly.

The methods further offer a low cost alternative for expensive microarray computing systems and non-integrated systems. The methods replace costly and non-efficient methods with a more affordable approach for both academic and industrial settings. Specifically, the use of one integrated process capable of controlling the image acquisition system as well as the analysis of the microarray images offers significant benefits of automation and accuracy. The present methods produce a streamlined workspace, allowing task integration of the various processes required to accurately analyze microarray data.

The methods provide a robust microarray computing system for obtaining data with superior quality and experimental results. Specifically, the image acquisition process provides higher quality images due to improved noise correction mechanisms and tightly integrated hardware and software components. Consequently, higher quality images are examined providing the automated tools a better analytical input for giving the user more reliable and accurate results. In addition, important experimental results associated with statistical values are provided with a higher degree of confidence.

The methods also provide flexibility. Although the above-described methods operate as a fully automatic analytical process, the user may intervene if necessary at any stage of the process, for correcting spot segmentation, conducting spot identification, or performing automatic exclusion of debris. Such flexibility for the user at any stage of the image acquisition and analysis process can provide higher yield by rescuing poor quality chips, e.g. with many missing spots, physical damage to spots, or a lot of debris.

Unless otherwise defined, all technical and scientific terms used herein have the same meaning as commonly understood by one of ordinary skill in the art to which this invention belongs. Although methods and equipment or software similar or equivalent to those described herein can be used in the practice of the present invention, suitable methods, equipment, and software are described below. All publications and other references mentioned herein are incorporated by reference in their entirety. In case of conflict, the present specification, including definitions, will control. In addition, the materials, methods, and examples are illustrative only and not intended to be limiting.

The invention provides numerous advantages as described above. Other features, objects, and advantages of the invention will be apparent from the description and drawings, and from the claims.

DETAILED DESCRIPTION

As described below, methods and systems of obtaining a corrected image of a microarray include acquiring an image of a microarray including a target spot, processing the image to correct for background noise and chip misalignment, analyzing the image to identify a target patch, edit debris, and correct for ratio bias, and detecting single copy number variation in the target spot using an objective statistical analysis that includes a t-value statistical analysis.

Figure 1:
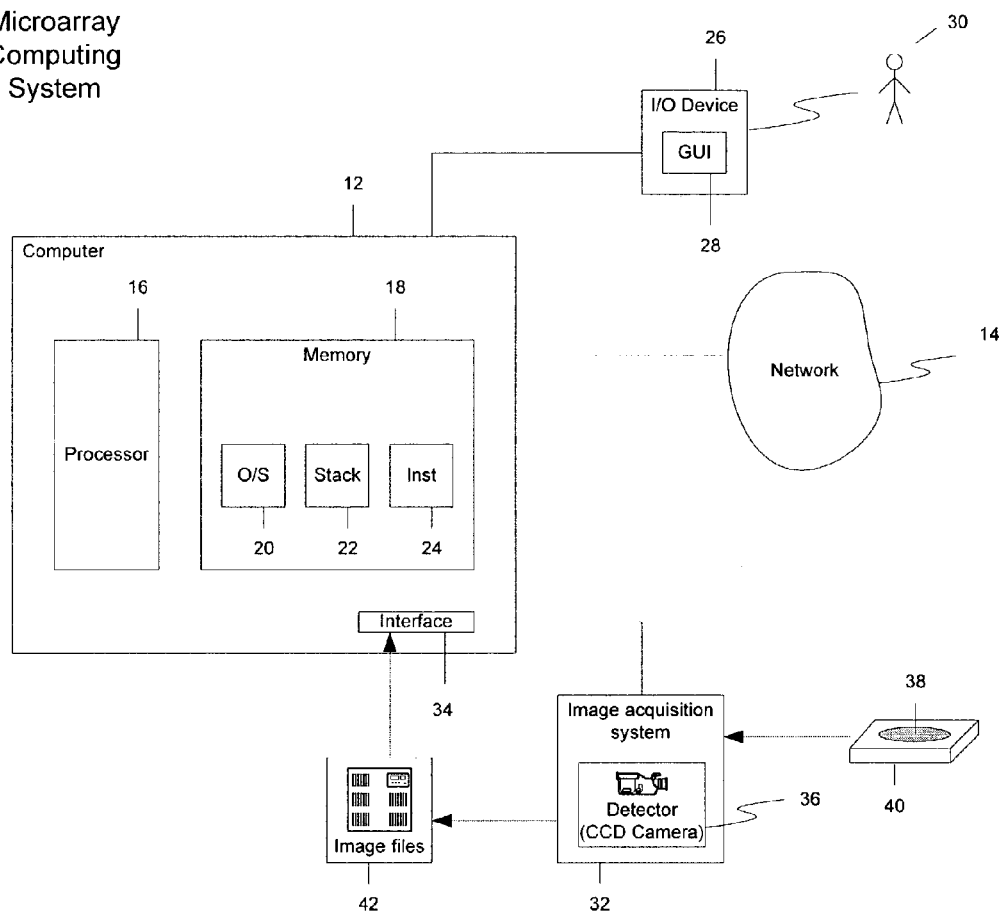
FIG. 1 is a schematic diagram of a computerized system for processing and analyzing genomic microarrays.

Referring to FIG. 1, a microarray computing system 10 includes a computer 12 such as a personal computer (PC) or workstation (e.g., an IBM PC). The computer 12 is connected to a network 14, such as the Internet, that runs TCP/IP (Transmission Control Protocol/Internet Protocol) or another suitable protocol. Connections may be via Ethernet, fiber, wireless link, telephone line, and the like.

The computer 12 contains a processor 16 and a memory 18. Memory 18 stores an operating system ("OS") 20 such as Windows98® or Linux, a TCP/IP protocol stack 22 for communicating over network 14, and machine-executable instructions 24 executed by the processor 16. Computer 12 also includes an input/output (I/O) device 26 such as a computer monitor for display of a graphical user interface (GUI) 28 to a user 30.

The microarray computing system 10 identifies specific changes in genomic characteristics. In particular, the microarray computing system 10 provides various processes related to processing and analysis of image files such as an image file 42 residing in the microarray computing system 10.

The computer 12 is connected to an image acquisition system 32 via an interface 34. The interface 32 uses a driver (not shown) to communicate with the processor 16 and the memory 18 of the computer 12. The image acquisition system 32 includes a detector 36, preferably a charge-coupled device (CCD) camera, although any suitable image acquisition device such as a laser scanner can be used. By way of example, the image acquisition system 32 captures an image of a microarray 38 on a substrate 40, e.g., a slide or chip such as a "DNA chip."

The precise nature of the detector 36 is not critical provided that the image file 42 provides three independent two-dimensional images for blue, green, and red fluorescence in suitable registration with each other. However, the quality of the images should be a primary consideration when choosing the image acquisition system 32. A CCD camera detector 36 offers simultaneous acquisition of relatively large images, e.g., of approximately 1 cm². Thus, irrespective of the detector 36 used, the image file 42 produced by the image acquisition system 32 is preferably generated by a high quality image acquisition system 32.

The image file 42 is fed to the computer 12 of the microarray computing system 10 for processing and analysis. Generally, the user 30 enters information into the microarray computing system 10 regarding fabrication and processing characteristics of a given microarray. Optionally, the microarray computing system 10 can obtain information regarding a specific genomic material from an external or internal database residing in a storage device via network 14.

Figure 2:
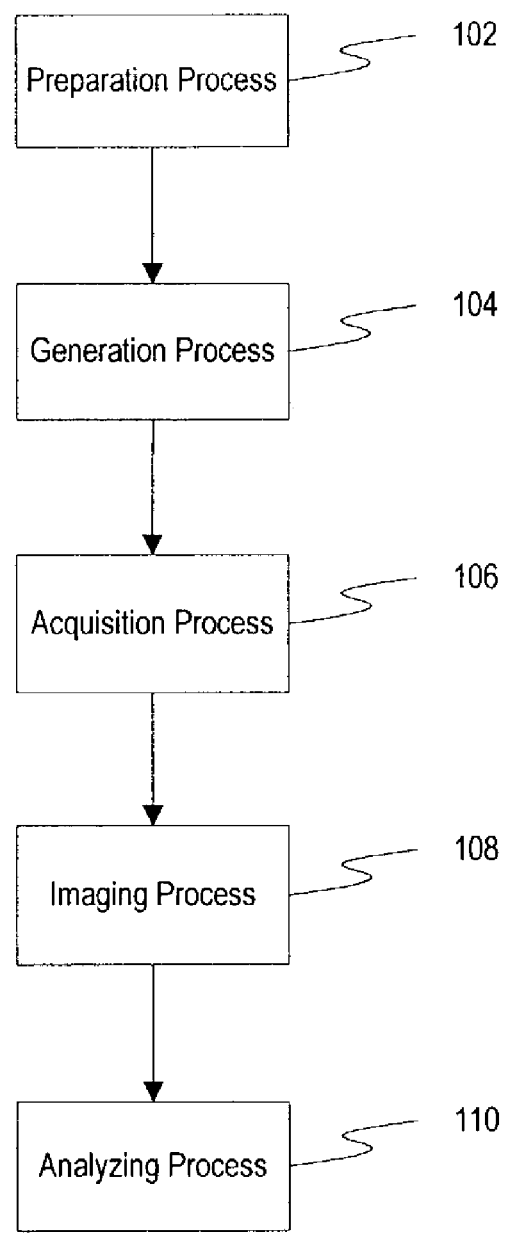
FIG. 2 is a flow chart of a microarray detection process.

Referring to FIG. 2, a genomic microarray detection process 100 includes preparing a material, e.g., a genomic material such as DNA in a preparation process 102. The prepared DNA is used for generating DNA spots in a microarray in a standard generation process 104. In certain embodiments, first, many different probe DNAs are selected, prepared, and printed on the microarray substrate. Typically, these various different probe DNAs can be printed on many microarrays at once. Each probe represents approximately 100 kbp, or $\frac{1}{30,000}^{th}$ of an entire genome. Moreover, each probe may be printed as several replicate spots. Secondly and arbitrarily later, whole genome DNA from the sample of interest (i.e., "test DNA") is prepared, fluorescently labeled, and hybridized to the DNA spots on a single microarray. Reference DNA is prepared, differently labeled, and simultaneously hybridized to the DNA spots. Subsequently, the microarray 38 can be imaged.

In operation, the genomic microarray detection process 100 further includes acquiring an image of the microarray in an acquisition process 106, and processing the image in an image pre-processing process 108. Subsequently, the genomic microarray detection process 100 provides an analyzing process 110 where the resulting image is statistically analyzed.

In describing the present embodiment, we follow a nomenclature convention where the spots of the immobilized genetic material on the microarray are referred to as a target and the whole-genome labeled DNA a probe.

Figure 3:
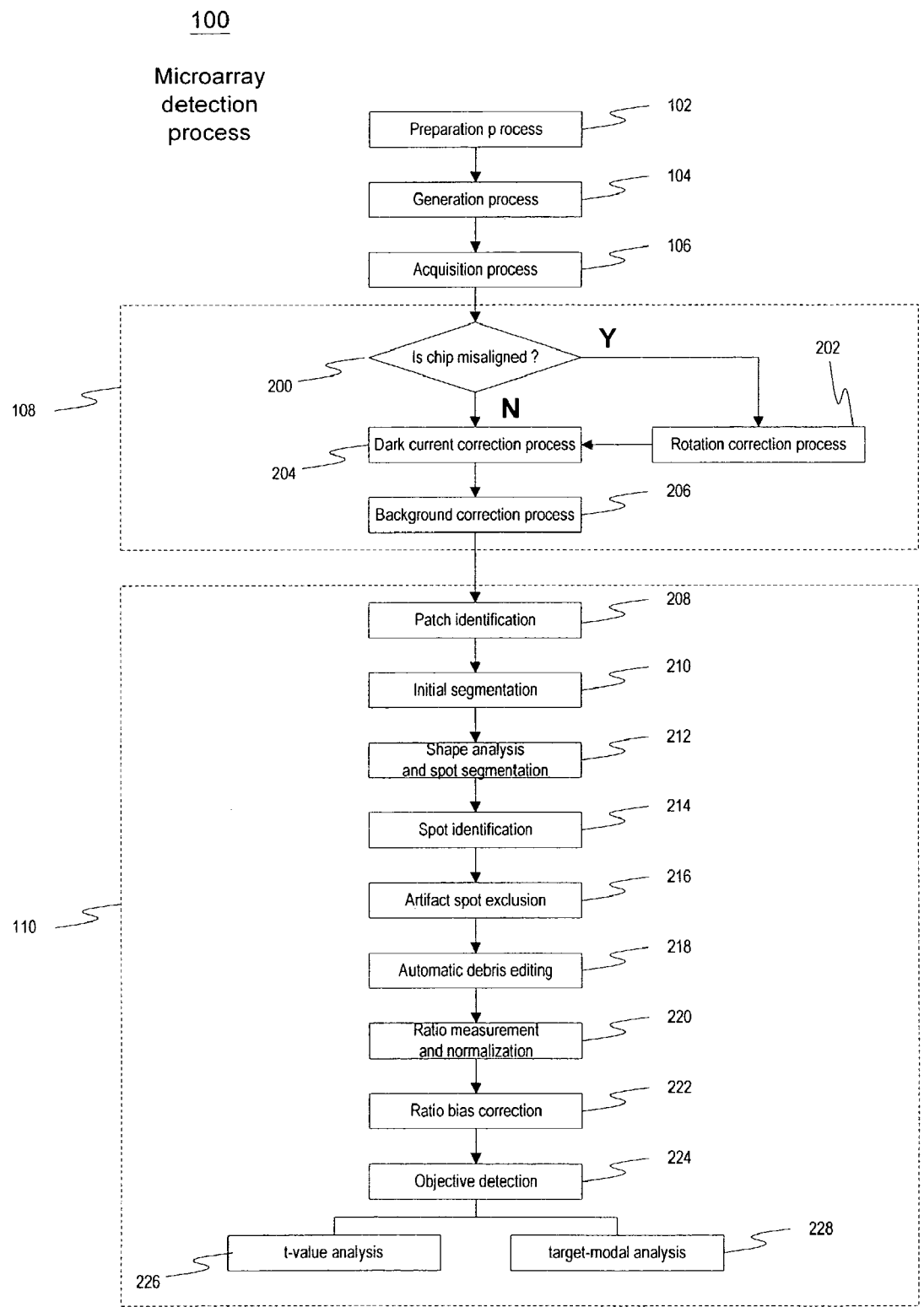
FIG. 3 is a flow chart of a more detailed view of the microarray detection process.

FIG. 3 illustrates a detailed view of the microarray detection process 100. The microarray detection process 100 begins with the preparation process 102 of preparing the probe genomic material. The preparation process 102 includes the manufacture of the microarrays. The labeling and hybridization of the microarray of the sample and reference DNA then separately follows.

The generation process 104 for generating array spots follows. Genomic microarrays include spots of targets, e.g., DNA arrayed regularly on a solid substrate such as glass, membranes, or metal. In certain embodiments, each DNA spot can represent a small contiguous region of a genome. The range of a genome is between 50 kbp (kilo base pairs) to 200 kbp in length. Such large-sized arrays are available, for example, from Vysis, Inc., of Downers Grove, Ill. Using larger sized genomic probes than complimentary DNAs (cDNAs) provides more sensitivity to gain or loss of a single copy of the corresponding DNA from the sample and therefore better results in the subsequent image pre-processing process 108 and analyzing process 110.

Additionally, generating the array spots in the generation process 104 includes preparing a suitable microarray substrate to form the array spots. Accordingly, a microarray must be designed, incorporating data such as layout information for spot density and spacing between adjacent spots, and, more importantly, information about the genomic material placed at each spot on the microarray. The microarray configuration may include the number and type of pins that deposit the spots the number of pin cleaning cycles, and the like. Some of the information required are parameters needed to configure the arrayer, and some are for tracking and logging purposes.

Microarrays are typically formed by robotically depositing targets in a regular pattern on the solid substrate. The rigidity of glass substrates and its desirable optical characteristics are preferable, but other types of substrates can be used. Glass slides can be coated before use to increase the binding efficiency of target material. A common coating used is chromium, used for binding to glass through nonconvalent linkages involving the primary amines of the lysine residues.

In the generation process 104, specialized robotic instruments use capillary tubes, piezoelectric ink-jets, solid pins, or pin-and-loop systems to deposit the target genetic material to the target spots. Another design uses slotted steel pins to transfer the target material from a source plate to the slide. Much like a quill pen, these slotted pins collect the probe by capillary action and then deposit small aliquots of it each time they contact the slide surface. Each pin typically takes up 0.1-0.6 µl (microliter) of genomic solution from the source plate depositing approximately 0.3-1.0 nl (nanoliter) as the array spot. Depending on the length of the genomic material, a significantly large number of DNA or genomic spots can be generated from a single loading of the pin, although in practice this number can be limited by factors such as evaporation or by the total numbers of slides that can be positioned on the robotic instruments. After the microarray substrate 40 is rinsed and dried, the substrate 40 is now ready to be hybridized with marked receptors. The microarray substrate can be optionally diced into smaller chips.

Preferably, the microarray is manufactured so that each target is represented by several replicate spots. The expectation that each of these spots should have the same test-to-reference intensity ratio provides redundancy that can be exploited to detect and reject artifacts, as well as to place a confidence interval on the estimated copy number ratio.

In addition to test and reference hybridization, usually green and red respectively, the spots are also counterstained with a blue DAPI color. Specifically, it is necessary to acquire an image at both the green and red wavelengths to generate a composite microarray image representing both fluorescent colors.

Following the sample preparation and hybridization processes of the processes 102 and 104, the microarray is ready to be scanned by the image acquisition system 32 in the acquisition process 106. The acquisition process 106 detects the hybridization results, i.e., the intensity of fluorescent signals.

Hybridization by fluorescent labeled, whole-genomic DNA results in signals on each target spot whose intensities are proportional to the copy numbers of the corresponding genomic loci. There are, however, substantial differences in signal intensities from spot to spot caused, for example, by the different targets containing different quantities of genomic material. A quantitative assay can be obtained by co-hybridizing with differently-labeled normal reference DNA which has known copy number, usually 2, and taking the ratio of "test" to "reference" signal intensities, in a manner entirely analogous to analysis of CGH. Thus, relative DNA copy numbers of the test sample at the represented genomic loci can be estimated. As with conventional metaphase target CGH, the absolute copy number cannot be determined without additional knowledge for calibrating the copy number of at least one of the loci.

Once the image of the microarray 38 has been captured and stored in memory 18 of the computer 12 of the microarray computing system 10, the acquisition process 106 outputs the image file 42. The image file 42 indicates, in the case of fluorescent labeled receptors, the fluorescence intensity, i.e., photon counts or other related measurements, such as voltage, as a function of position on the substrate. Since higher photon counts will be observed where more of the labeled DNA sample has bound to a genomic target on the microarray, and since the amount of DNA which binds to a target is related to the copy number of the DNA at the corresponding genomic locus, it is possible to determine change at the single copy level of the genomic material as well as the relative copy numbers of the sample at different loci from an objective analysis of this data.

Once the microarray 38 is placed in the detector 36, the image pre-processing process 108 includes checking (200) a holder of the detector 36 for microarray misalignment caused by incorrect alignment of the substrate chip with the chip carrier. This causes rotation of the spot grid by an angle, which can in extreme circumstances cause mis-identification of rows and/or columns of the spots. In the image pre-processing process 108, if a microarray is misaligned, an automatic detection and image rotation correction process 202 is performed. The angle of rotation, if any, can be measured automatically by precise location, to sub-pixel accuracy, of a maximum of the power spectrum of the image corresponding to the basic spot spacing. If the angle is relatively large (e.g., greater than 1°), the whole image could be rotated to compensate for the misalignment.

Image rotation correction processes requires the computation of pixel values in the rotated image from the original pixel values in the original image. Known rotation correction processes methods exist, e.g. nearest neighbor, bilinear interpolation, bicubic interpolation, etc., some providing better accuracy than others at the expense of slower operation and more complex coding. In the present embodiment, the automatic detection and image rotation correction process 202 includes bicubic interpolation between the values of the four nearest pixels.

Whereas the primary constraint of the acquisition process 106 is data quality, the most important consideration in the image pre-processing process 108 and the subsequent analyzing process 110 is data analysis. Thus, obtaining the best possible "raw" image is critical for the acquisition process 106. This avoids compensating for the image acquisition system 32 inadequacies by processing the image in software. However, image processing cannot be entirely avoided. After the automatic detection and image rotation correction process 202 is performed, two image correcting processes are performed: a dark current correction process 204 and a background correction process 206.

Dark current is noise present in the absence of light input. Dark current is measured in electrons per second and is introduced by any photon-detecting device such as CCD cameras and scanners. This noise originates from thermal emissions from the photosensor such as photocathodes, and/or leakage current. Although in a properly designed system, noise can be eliminated, noise is initially present in all optical measuring systems. Because the quality of the raw image is critical for accurate microarray quantitation, an important goal is to maximize the signal-to-noise ratio.

The signal-to-noise ratio quantifies how well a true signal from the noise of a microarray scanning system can be resolved. It is typically computed by taking the peak signal divided by the variation in the signal. If the microarray scanning system has a poor signal-to-noise ratio, the variation in the signal alone can prevent accurate quantitation of each spot. Combining an integration duration of, for example, 5 seconds, a CCD camera gain of 4, and signal intensities of approximately 1/10 of the CCD dynamic range, dark current caused by capture in the CCD wells of thermally excited electrons can be significant.

In the dark current correction process 204, dark current is corrected by capturing a dark image with the same exposure time and subtracting it from the image. In order to prevent negative pixel values, a constant positive bias of approximately 1% of the CCD dynamic range is added to every pixel of the image. In the dark current correction process 204, per-pixel dark current bias is removed at the expense of an increase, by a factor of the square root of two, in the noise component caused by a random variation in the dark current noise.

The imaging process 108 includes a background correction process 206. To reduce the effect of nonspecific fluorescence, such as autofluorescence of the glass slide or nonspecific binding of test and reference genomic mixtures, the background correction process 206 is performed. In particular, background noise is caused by stray light, autofluorescence of the cover slip and/or objective lens, and non-specifically bound fluorophore on the slide surface. For these, it is reasonable that the effects are constant or vary smoothly across the image, Therefore, the background noise level between spots can provide a reliable estimate of the background noise contribution to the total signal level within a spot. Background noise is particularly harmful because it significantly adds bias distorting the spot ratio computation. Consequently, background noise subtraction is critically important to spot quantitation.

Background correction can be performed by first determining the local background intensity and then subtracting this from the image. In the background correction process 206, background noise is corrected by computing a background image and subtracting it from the original image. The background correction process 206 causes the corrected image to have more contrast and the image directly correlates to the actual measurements made.

Figure 4:
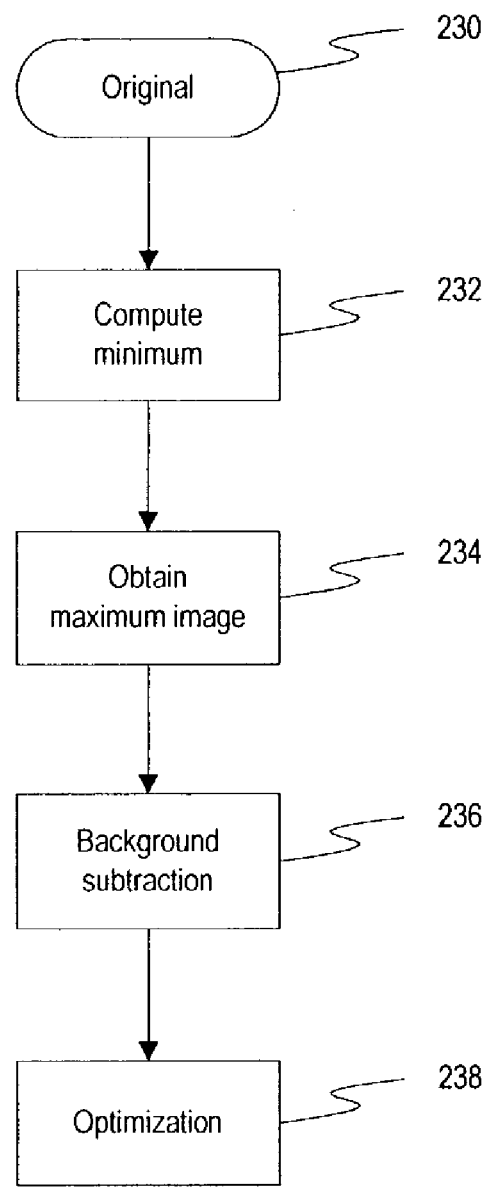
FIG. 4 is a background correction process.

Specifically, referring to FIG. 4, in the background correction process 206, after the original image is obtained (230), the original image is smoothed (232) and the background noise is estimated by computing a minimum value of the smoothed image (234) and computing a maximum image of the minimum image, i.e., the background image (236). In the computation for the minimum image, the minimum transformation is computed on an image that results from convolving the original image with a 5×5 uniform smoothing filter. In this example, this reduces the noise excursions on average by a factor of 5, resulting in an improved estimate.

Subsequently, the background image is subtracted from the original image (238). An optimization process (239) follows where an image mode is subtracted to obtain the "background corrected image." In the optimization process (239), the background peak of the pixel intensity histogram of the resulting image is identified and its value further subtracted from the corrected image, guaranteeing that in the corrected image, the background has a mean value of zero.

Because higher frequency random noise in the image is not reduced by background correction, the background-corrected image has pixels of negative values. Truncating negative pixel values to zero would impose a significant bias on spot intensity quantitation. Therefore, the background-corrected image includes signed pixel values.

Hereinafter, unless otherwise indicated, all images have been background corrected by the background correction process 206.

Referring back to FIG. 3, once the microarray image has been processed and corrected for the various image acquisition anomalies during the image pre-processing process 108, the analyzing process 10 is carried out on the image file 42.

However, before numerical computation and substantive data analysis can be performed, an objective identification of pixels representing signals and nonsignal intensities is necessary. Thus, a process 208 of patch identification and processes 210, 212 and 214 leading to spot identification follows.

Most large size chips are formed with several patches of spots printed onto the solid substrate. A patch is a collection of DNA spots printed in a regular two-dimensional grid pattern uniformly positioned separately from other similar patches. Commonly, each patch is printed by one pin of a multi-pin printer. Identifying the patches in the image limits the region of the image where valid spots may occur, increasing resilience to debris. Patches also provide a set of origins for spot identification, increasing resilience to missing or artifactual additional spots, and to possible displacement of a subset of the spots caused by misalignment of a particular pin of a multi-pin printer.

Figure 5:
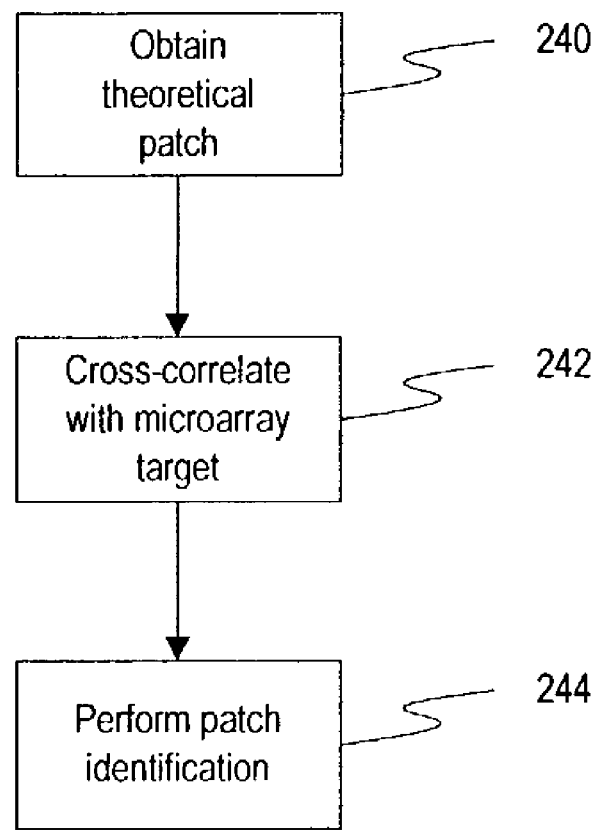
FIG. 5 is a patch identification process.

FIG. 5 illustrates the patch identification process 208. First, a theoretical specification of a set of patches is obtained (240) from a file, database or another suitable techniques. Second, the image generated from the theoretical set of patches is then cross-correlated (242) to the DAPI counterstain image, i.e., the blue image of the microarray. Third, the result is definitive localization of the set of patches in the image, from which consequently, patch identification is performed (244).

Referring back to FIG. 3, following the process 208 of patch identification, the analyzing process 110 includes an initial segmentation process by threshold 210. In the initial segmentation process by threshold 210, a threshold is computed by analyzing the pixel intensity histogram of the DAPI counterstain image. Accordingly, a set of above-threshold pixels is obtained, and this set can be further processed by masking it by a set of patches. Thus, debris lying outside of the patches is immediately rejected.

A spot shape analysis and spot segmentation process 212 follows. Although the set of above-threshold pixels within the patches mainly represents the spots, spot identification can be markedly improved by performing additional processes based on knowledge of expected spot shapes.

There can be notable variations of signal intensity due to the heterogeneity of the deposition of DNA during the microarray printing process 102. In other words, with the acquisition process 106, it is possible to have features that show a "doughnut" or "coffee ring" appearance, with strong fluorescence on the perimeter of the spots and dim fluorescence in the center, or irregular borders. Thus, printed spots have a circular "coffee ring" shape and the above-threshold pixels form a closed ring, or more infrequently, a ring with an opening, i.e., a "C-shaped" ring.

In the spot shape analysis and spot segmentation process 212, the set of above-threshold pixels is first opened by performing erosion followed by dilation. This effectively removes tiny pieces of debris in thin filaments and/or debris lying between the spots. Subsequently, the remaining set of pixels is segmented by finding the connected sets of pixels. Each connected set of pixels, referred to as a "spot object," is potentially a spot.

The spot forms obtained as described above can be improved by replacing a smaller spot object, by pixel count, by its filled convex hull, i.e., minimum enclosing convex polygon, or by simply filling larger spot objects. Since these operations may join previously separate spot objects, the revised set of spot objects must be re-labeled into a new set of connected components.

The spot shape analysis and spot segmentation process 212, thus results in filled, mostly convex spot objects, each of which is usually a single spot. Adjacent spots can occasionally be joined, often due to intervening above-threshold debris. Pairs of joined spots having "dumbbell-shaped" forms are explicitly recognized and separated at their "waist" into two spots. Other "very large" spot objects having larger than 4 times their expected spot area are entirely removed from the set of spot objects, as described in later analysis.

The analyzing process 110 can further include a spot identification process 214. Before calculations are performed, a determination is made concerning which spot objects represent probe spots and which spot objects represent debris or other artifact.

A set of spot objects, i.e., connected sets of above-threshold pixels modified by all of the processes described above 212, mostly includes the spots to be analyzed. There may, however, be additional spot objects as a result of fluorescent debris. Moreover, one or more spots may be missing from the microarray on account of physical damage, or missing on account of very low fluorescence intensity.

Therefore, in the spot identification process 214, the set of spot objects is optimally matched to a theoretical grid of spots using a constrained relaxation classifier where each spot is allocated to a grid point and after an initial "guess" is made for the assignment of spots to a grid point, various "constraints" are added. Constrained relaxation classifier is a robust pattern recognition approach involving a spot allocation framework to classifier points such as grid points, which iteratively estimates the best possible identification of spots. Each iteration is updated, complementing each other in correctness, and relaxed to arrive at the best obtainable figure of merit.

Examples of constraints include assigning only one spot to one point on the grid, allocating only one spot to a grid point, or allocating the spots to grid points that are "as close as possible." In a constrained relaxation classifier, initial set of allocations is analyzed for inconsistencies, and an overall figure of merit obtained. The grid positions (rows and columns) are evaluated nudged and the constrained relaxation classifier processed repeated until the set of allocations converges to a "best" or highest obtainable figure of merit and correct solution.

Thus, spots are matched to their closest grid location. As described above, the classifier iterates to optimize a measure of the overall fit of the segmented spots to the specified grid.

Consequently, identification of most and very often all of the spots results from the spot identification process 214. Unidentified spots are not used in any further processes of the analyzing process 110. Similarly, grid locations in the microarray without an assigned spot do not contribute further to the analysis of the corresponding target.

The analyzing process 110 includes an artifact spot exclusion process 216. Although readily and positively identified, spots may show by their appearance that they may not provide reliable measurements. For instance, spots that are too large, too small, or are significantly elongated are automatically excluded from further analysis.

Figure 6:
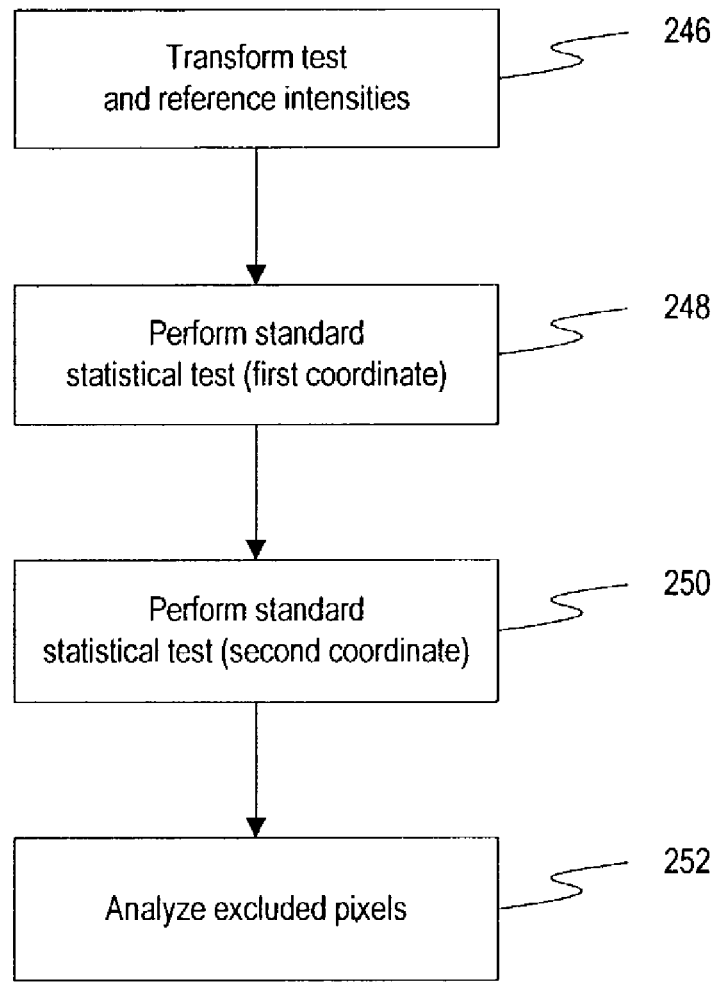
FIG. 6 is an automatic editing process for image debris.
Figure 7:
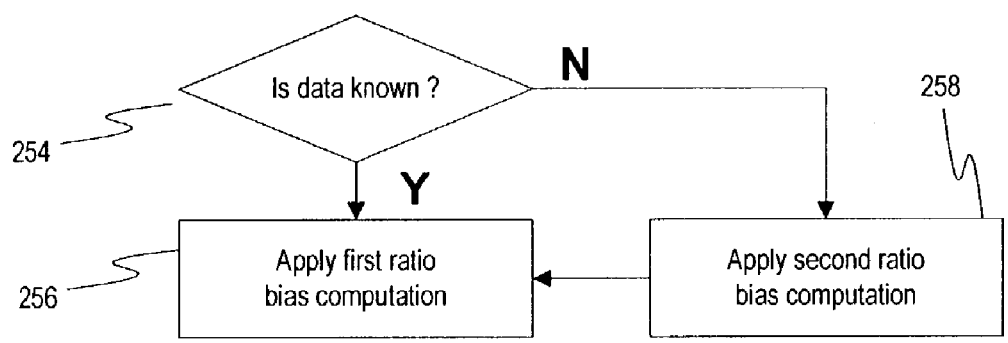
FIG. 7 is a ratio bias correction process.

Following the artifact spot exclusion process 216 and referring to FIGS. 3 and 6, the analyzing process 110 further includes an automatic debris editing process 218. Spots may contain debris that cause unreliable measurement although not impacting the spot's shape sufficiently for the spot to be excluded by any of the processes of the analyzing process 110 discussed above.

The automatic debris editing process 218 removes spot debris by recognizing and excluding pixels within a spot having outlying intensity or ratio compared with the majority of the pixels of the spot. Referring to FIG. 6, in a first step (246), the automatic debris editing process 218 includes the pixel test and reference intensities transformed to polar coordinates corresponding to the overall intensity (radius coordinate) and the ratio (angle coordinate) of each pixel in the spot. In a second step (248), a standard statistical test for outliers is applied to the intensity axis, i.e., the radius coordinate which denotes pixel intensity. Similarly, the same standard statistical test is performed (250) on the remaining pixels for the angle coordinate which denotes the pixel ratio. Thereafter, the shape of the set of excluded pixels is analyzed (252) so that pixels spatially adjacent to a significant "blob" of outliers can further be recognized and excluded.

Referring to FIG. 3, the microarray analyzing process 110 includes a ratio measurement and normalization process 220. In the ratio measurement and normalization process 220, a ratio computation is performed to obtain a spot's "raw" ratio. The "raw" ratio is defined as the ratio of total test, e.g., green fluorescence intensity, such as a Alexa green labeled probe prepared from a test tissue, to a total reference, e.g., red fluorescence intensity, such as a Alexa red labeled probe prepared from a reference tissue. Total fluorescence is the sum of background-corrected pixel values for all the non-excluded pixels within the spot, i.e., the sum of the intensity values of all the pixels in the signal region. The total intensity is sensitive to variations in the amount of DNA deposited on the surface of the microarray, the existence of contamination, and anomalies in the acquisition process 106.

Fluorescence intensities depend on a variety of factors such as labeling efficiency, fluorophore quantum efficiency, CCD quantum efficiency at given wavelengths, exposure time, CCD camera gain, filter pass bandwidth, attenuation, and the like. These factors are not determined with sufficient accuracy to compute a standardized intensity. Therefore, the set of raw ratios for every spot of the chip 40 is normalized, preferably using the median of the raw ratios, although techniques of normalization using the mean of the raw ratios or the mode of the raw ratios may also be used. For normalizing the ratio using median values, every raw spot ratio is divided by the median of the raw spot ratios. As a result of this normalization, the median raw spot ratio is itself transformed to 1.0. Median intensities are often preferred over arithmetic mean intensities because median intensities are less susceptible to extreme values at either end of a distribution. The relevant measure is the median of all the spot intensities, computed as specified above, i.e., total green intensity divided by total red intensity. Thus, normalization eliminates experimental variations.

After normalization of the signal intensity data in the process 220, a ratio bias correction process 222 is carried out. When a set of targets on the DNA chip is hybridized by normal test and reference DNAs yielding supposedly equal ratios from all spots, it is sometimes observed that the ratios are in fact greater in the less bright spots than in the brighter spots. This phenomena is known as "ratio vs. intensity bias" (bias). Possible explanations for this phenomena may include green autofluorescence or the occurrence of a different level of background "under" the spot as compared to "between" the spots. Green autofluorescence relates to a contribution to the spot intensity inherent in the spot which is unrelated with the level of test DNA hybridization.

The model for the bias can be initially characterized as:

$$R=(t+A_t)/(r+A_r) \qquad (1)$$

where R represents the measured ratio of a spot, t denotes the total test fluorescence intensity, r denotes the total reference fluorescence intensity resulting from the hybridization, and $A_t$ and $A_r$ represent the non-hybridization autofluorescence for the test and reference signals, respectively. From this computation, variations from target to target are observed. Because $A_t$ is typically greater than $A_r$, R increases with reduction of the hybridization intensity.

It is inefficient and almost impossible to measure and compensate for each per-target autofluorescence intensity. The ratios for spots of modal copy number targets are consistent with a curve according to the following equation:

$$R=1.0+\log(1.0+B/r) \qquad (2)$$

where R denotes the ratio, r the reference intensity, and B a non-negative constant.

Equation (2) is used within a normalized constant of proportionality. The ratio bias correction process 222 first estimates a value for B, then uses the value for B to apply a suitable compensation.

The ratio bias model based on equation (2) above follows the observed shape of the bias including the asymptotically constant ratios of higher reference intensities. Moreover, correcting the ratio bias according to equation (2) requires estimation of a single parameter B as opposed to a linear fit having two parameters or a quadratic fit having 3 parameters to the observed bias. Consequently, the ratio bias correction process 222 based on equation (2) provides a superior computation for estimating ratio values.

However, the optimization of B in equation (2) can occasionally be disturbed by local minima. More robust bias correction is obtained by optimizing the non-negative constant B in an alternative formula that also closely fits the observed shape of the bias:

$$R = r^{-B} \quad (3)$$

Equation (3) is a model for the observed bias in modal target spots, again within a constant of normalization, with 0<=B<=1.0. Consequently, equation (3) provides the preferable computation for correcting ratio bias in a stable optimization.

Ratio bias correction of unknown data is performed using a selection of "plausibly modal" spots whose normalized ratios are close to 1.0 (in the range 0.7 to 1.4), A value of B is chosen which minimizes the mean square difference between the set of normalized original ratios $R_{original}$ and the set of normalized predicted ratios $R_{predicted}$ according to equation 3. The bias corrected ratios, then, for all the spots (not just those selected above) are computed as follows:

$$R_{corrected} = R_{original}/R_{predicted} \quad (4)$$

Figure 8A:
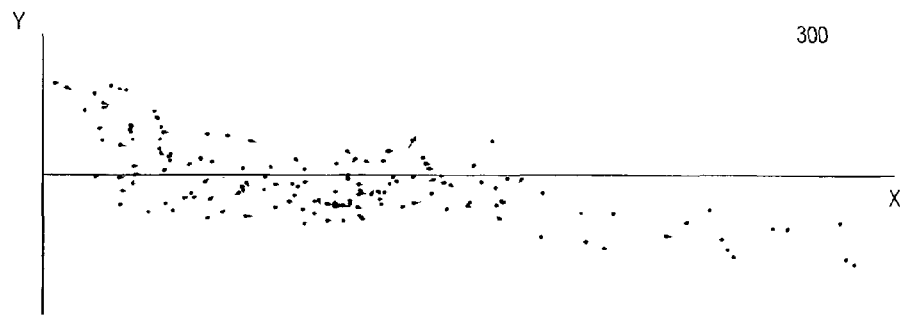
FIG. 8 is experimental results of the ratio bias correction process of FIG. 7.
Figure 8A:
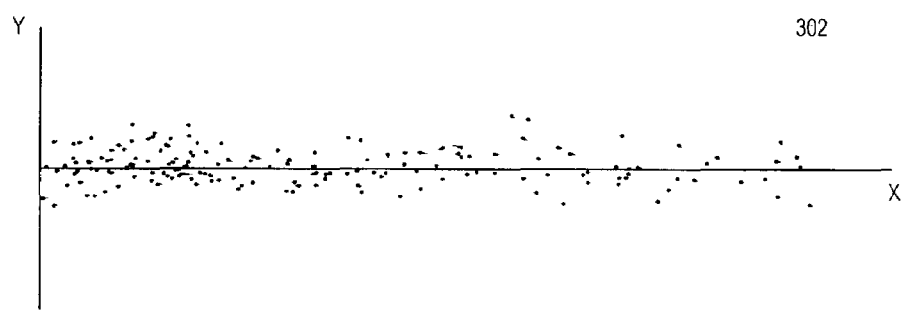
Figure 8B:
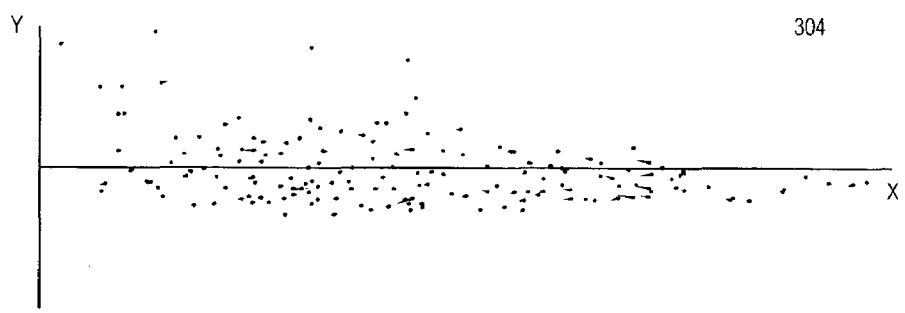
Figure 8B:
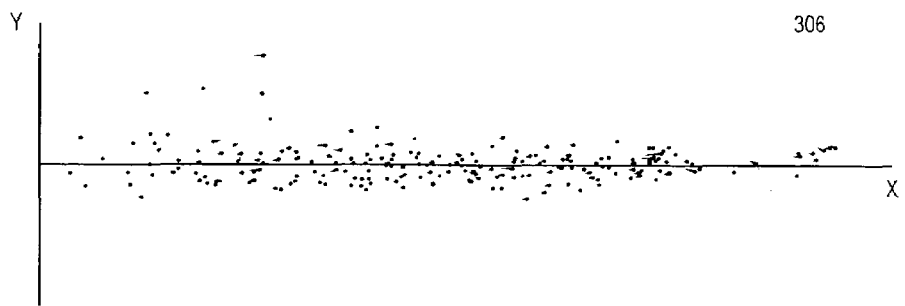

The experimental results of the ratio bias correction process 222 are shown on FIGS. 8a and 8b. FIGS. 8a and 8b show exemplary graphs of normalized ratios for each spot plotted against its reference intensity. FIG. 8a shows an extreme case of bias whereas FIG. 8b shows a case of lesser bias.

Referring to FIG. 8a, in the first graph 300, the y-coordinate represents a normalized non-bias corrected ratio for each spot and the x-coordinate represents the spot's corresponding reference intensity. In contrast, in the second graph 302, the y-coordinate represents a bias corrected normalized ratio of each spot. The bias corrected graph 302 shows a more stable and constant final plot than the graph 300 using the non-bias corrected ratio data.

Referring now to FIG. 8b, data having a lesser bias than in FIG. 8a was similarly plotted using the same coordinates as in FIG. 8a. Although only a relatively small bias was present, differences of the plots from the non-bias corrected graph 304 and the bias-corrected graph 306 are readily noticeable.

In comparing the graphs 300 and 302 from FIG. 8a and graphs 304 and 306 from FIG. 8b, the higher ratio values plotted in the graphs of FIG. 8a come from the X chromosome targets in a female vs. male hybridization. Thus, higher ratios are better discriminated from modal ratios following bias correction.

Following the ratio bias correction process 222, an objective detection process 224 for copy number change follows. Comparing novel normalized ratios to the theoretical value of 1.0 is not a sufficient basis for detecting copy number change because the mean target ratios obtained in normal vs. normal hybridizations are not equivalent to 1.0. Consequently, as shown in FIG. 3, the objective detection process 224 includes two alternative processes for comparing ratios and detecting copy number changes: a t-value statistical analysis 226 and a target-modal statistical analysis 228.

Figure 9:
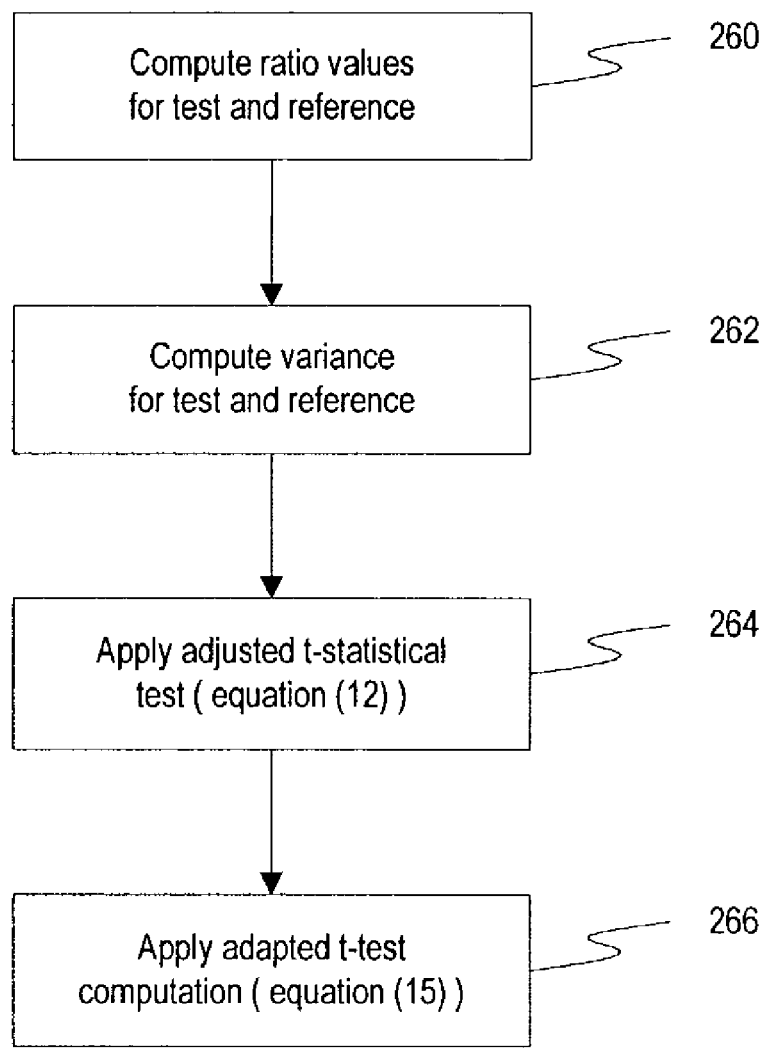
FIG. 9 is a process for a statistical t-value analysis.

Referring to FIG. 9, a t-value statistical analysis process 226 is shown. The t-value statistical analysis process 226 provides an objective mechanism for analyzing cases where the differences of modal target ratios from the theoretical normal ratio of 1.0 are consistent for a target from experiment to experiment.

Specifically, mean target ratios can be compared to the corresponding per-target mean in multi-chip calibration data thereby allowing adjustments for the consistent differences between targets in the normal vs. normal ratio.

The t-value statistical analysis 226 is based on the "Student's t-distribution," commonly referred to as the "t distribution". The t-test provides a statistical procedure for testing samples for a significant difference in means between two groups. The t-test generally computes a standardized value computed by dividing the difference in means between the two groups of data by its standard error, i.e., the standard deviation of the mean differences. In other words, if the variability of the measurements in two normal samples is equivalent, then they can be measured by a common variance $\sigma^2$. This means that both samples have exactly the same shape, and the variances are the same, i.e., $\sigma^2_1 = \sigma^2_2 = \sigma^2$. As a result, the standard error of the difference in the two sample means is represented by the following equation:

$$\sqrt{\frac{\sigma_1^2}{n_1} + \frac{\sigma_2^2}{n_2}} = \sqrt{\sigma^2\left(\frac{1}{n_1} + \frac{1}{n_2}\right)} \quad (5)$$

Mathematically, then, if the appropriate sample estimate $s^2$ for the population variance $\sigma_2$ is used, the resulting test statistic has a t distribution, as shown below:

$$t = \frac{(\bar{x}_1 - \bar{x}_2) - (\mu_1 - \mu_2)}{\sqrt{s^2\left(\frac{1}{n_1} + \frac{1}{n_2}\right)}} \quad (6)$$

What remains then is to find the sample estimate $s^2$ and the appropriate number of degrees of freedom for the t distribution.

For the t-value statistical analysis 226, a final t-value analysis is mathematically computed based on a number of statistical derivations.

A final t-value equation to be used in the present embodiment is derived by a number of computational processes as shown in FIG. 9. First, the ratio values for the test:reference and reference:reference hybridization are computed (260). Test:reference hybridization refers to an analysis in which the two hybridized DNA samples are derived from the test and reference genomic material and the reference:reference hybridization refers to an analysis in which the two hybridized DNA samples are both derived from reference materials.

The ratio for the test:reference $X_T(k)$ is as follows:

$$X_T(k) = \mu_T(k) + A_T(k) + B_T(k) \quad (7)$$

and the ratio for the reference:reference $X_R(k)$ is represented by:

$$X_R(k) = \mu_R(k) + A_R(k) + B_R(k) \quad (8)$$

where $\mu(k)$ represents the theoretical value (or true) for the ratios at a particular target (k), A(k) is a random variable, with mean zero and variance $\sigma_a^2(k)$ representing variation among means from different hybridizations, and B(k) is a random variable, with mean zero and variance $\sigma_w^2(k)$ representing variation among spots within each hybridization.

Next, variance values for test and reference data are computed (262) for the spots within each of the target. The values of the variance $\sigma_T^2(k)$ for the test:reference hybridization and the variance $\sigma_R^2(k)$ for the reference:reference hybridization are as follows:

$$\sigma_T^2(k) = \sigma_{Ta}^2(k) + \frac{1}{m_T}\sigma_{Tw}^2(k) \quad (9)$$

$$\sigma_R^2(k) = \sigma_{Ra}^2(k) + \frac{1}{m_R}\sigma_{Rw}^2(k) \quad (10)$$

Thereafter, a comparison of the test and reference spots is performed by comparing, for each position of the DNA, the mean of a single test:reference hybridization with the pooled mean from reference:reference hybridizations. However, the usual t-statistic cannot be used because the variance of the spot mean for a test:reference hybridization does not equal the variance of the spot mean for the reference:reference hybridization. Therefore, an alternate form of the t-value equation can be applied (264). The following equation is referred to as the adjusted t-statistical test:

$$t(k) = \frac{(\bar{x}_T(k) - \bar{x}_R(k))\sqrt{n_T + n_R - 2}}{\sqrt{\left(\frac{\sigma_T^2(k)}{n_T} + \frac{\sigma_R^2(k)}{n_R}\right)\left(\frac{n_T s_T^2(k)}{\sigma_T^2(k)} + \frac{n_R s_R^2(k)}{\sigma_R^2(k)}\right)}} \quad (11)$$

where $\bar{x}_T(k)$ refers to the test:reference spot mean for a target k; $n_T$ represents the number of test:reference spot means, usually 1; $\sigma_T^2(k)$ is the theoretical variance of test:reference spot means; $s_T^2(k)$ is the sample variance of test:reference spot means. In a similar fashion, $\bar{x}_R(k)$ is the mean of reference:reference spot means; $n_R$ is the number of reference:reference spot means, which must be more than 1; $\sigma_R^2(k)$ is the theoretical variance of reference:reference spot means; and $s_R^2(k)$ is the sample variance of reference:reference spot means.

Since the theoretical variances for $\sigma_T^2(k)$ and $\sigma_R^2(k)$ are unknown, the ratio of $\sigma_T^2(k)$ is assumed to be constant over all targets. Let $\theta = \sigma_T^2(k)/\sigma_R^2(k)$. The following equation for $\sigma_R^2(k)$ is then used to compute the values for $s_R^2(k)$ and $\sigma_R^2(k)$, $$\sigma_R^2(k) = \sigma_{Ra}^2(k) + \frac{1}{m_T}\sigma_{Rw}^2(k) \quad (12)$$

where $\alpha$ denotes variation among hybridization means. Subsequently, equations for computing $\theta$ and $s_T^2(k)$ are derived, as follows:

$$\theta = \frac{\text{med}[s_R^2(k)] - \frac{1}{m_R}\text{med}[s_R^2(k)] + \frac{1}{m_R}\text{med}[s_T^2(k)]}{\text{med}[s_R^2(k)]} \quad (13)$$

$$s_T^2(k) = \left[s_R^2 - \frac{1}{m_r}s_R^2(k)\right] + \frac{1}{m_T}s_T^2(k) \quad (14)$$

Finally, using equation (13) and equation (14), above, in combination with the adjusted t-statistical test, the final t-value equation used in the present computation is derived:

$$t(k) = \frac{(\bar{x}_T(k) - \bar{x}_R(k))\sqrt{n_T + n_R - 2}}{\sqrt{\left(\frac{\theta}{n_T} + \frac{1}{n_R}\right)\left(\frac{n_T s_T^2(k)}{\theta} + \frac{n_R s_R^2(k)}{1}\right)}} \quad (15)$$

Equation (15) is now applied to the ratio data (266) to arrive at the difference between the two samples, leading to the completion and end of the statistical data analysis. Moreover, the final t-value obtained from equation (15) is distributed as a central t-distribution with a suitable number of degrees of freedom. Preferably, in applying equation (15) to the ratio data, the results are reported as the significance or p-value of the difference between the measured mean ratio and the calibration data mean. A method for objectively interpreting comparative genomic hybridization (CGH) using these equations has been developed and is described in greater detail in Moore et al., "A t-Statistic for Objective Interpretation of CGH Profiles," Cytometry 28:183-190 (1997), published by Wiley-Liss, Inc.

Figure 10:
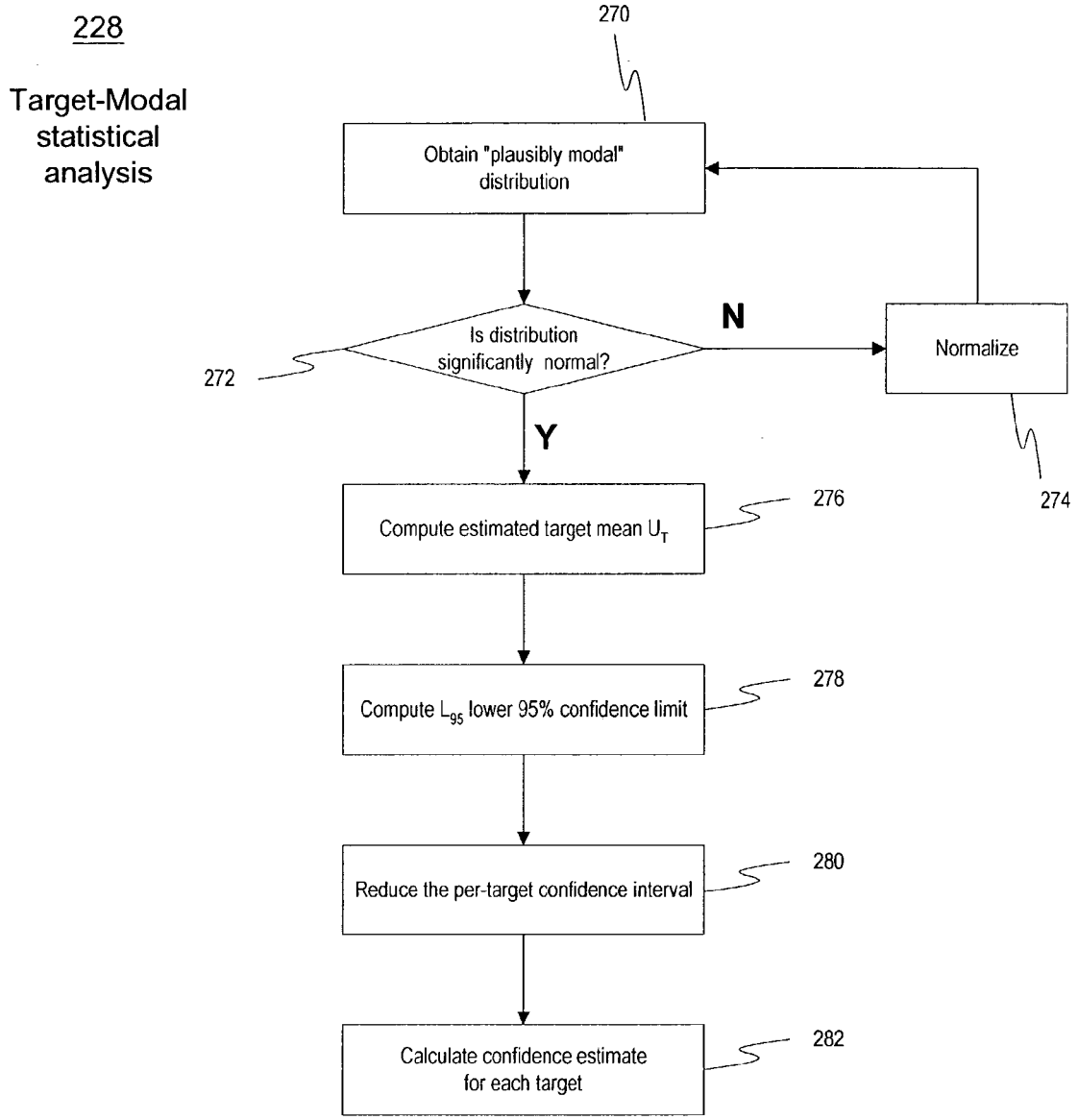
FIG. 10 is a process for a statistical target-modal analysis.

Referring now to FIG. 10, an alternate embodiment of the objective detection process 224, namely, a comparison of the target-mean to the distribution of modal targets analysis process 228, is shown. Unlike the t-value statistical analysis process 226, the comparison of the target-mean to the distribution of modal targets analysis process 228 does not require any reference or other data which is external to the analysis of a single chip. The comparison of the target-mean to the distribution of iodal targets analysis process 228 compares a target's confidence interval with the confidence interval of modal targets.

In particular, the comparison of the target-mean to the distribution of modal targets analysis process 228 includes comparing the mean and standard error of a single target with the distribution of all targets whose copy numbers are "plausibly modal," i.e., believed neither to be gained nor lost. The comparison of the target-mean to the distribution of modal targets provides a probability value for a significant change that is reasonably "honest".

Figures 11, 12:
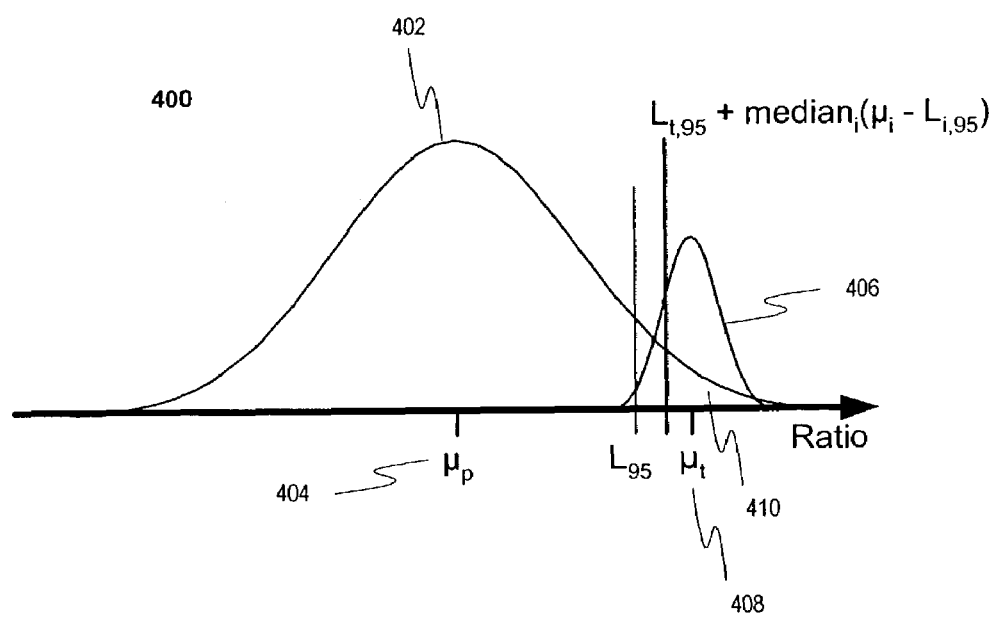
FIG. 11 is experimental results of false positive counts
FIG. 12 is a graphical plot of the statistical analysis of FIG. 10.

Furthermore, the computations associated with respect to FIGS. 10-12 use log-ratios since the distributions may be significantly skewed by random noise in ratio-space, but are unskewed in log-ratio space.

Referring to FIGS. 10-12, the comparison of the target-mean to the distribution of modal targets analysis process 228 includes identifying the plausibly modal targets and measuring the mean and standard deviation of their distribution. This distribution is shown by a distribution curve 400 in FIG. 12.

FIG. 11 illustrates experimentally the numbers of false positives detected at different confidence levels by the comparison of the target-mean to the distribution of modal targets method. In this context, a false positive is a target which has modal DNA copy number but has been identified as having non-modal DNA copy number. At any given confidence level, i.e., p-value, it is expected that a certain number of false positives is present. If the p-values computed by the procedure are "honest," the number of false positives closely match the number predicted by the confidence value. For example, it can be predicted that one out of every one hundred modal targets will be false positive with p<0.01, while only one out of every one thousand modal targets will be a false positive with p<0.001. In an exemplary spot segmentation and identification applied, false positive targets observed at different probability thresholds were obtained and a comparison made between the number of observed targets to the number of targets predicted from the probability thresholds. FIG. 11 shows the observed and predicted false positives in a set of 10 chips each with 191 targets, 180 of which should have shown modal copy number results. As illustrated in FIG. 11, the modal distribution has less extended tails and a higher kurtosis than the fitted normal distribution. Nevertheless, the probability estimates are shown to be relatively honest.

The comparison of the target-mean to the distribution of modal targets analysis procedure is as follows. $\mu_t$ is the estimated mean ratio for a target, computed (276) from the replicate DNA spots for the target. If $\mu_t$ is greater than one (indicating the likelihood of a gain of copy number), the lower 95% confidence interval limit of $\mu_t$ is computed using a t-distribution. Thus, the lower 95% confidence limit is computed (278). $L_{95}$, as shown in FIG. 12, denotes the lower 95% confidence limit for $\mu_t$. Therefore, the target's true ratio is greater than $L_{95}$ with 95% confidence.

Since there is a 95% confidence that the reported probability is an overestimate of the true probability, the reported probability can be made substantially more realistic by an optimization process. Specifically, the per-target confidence interval is reduced (280) by the median per-target confidence interval over all targets. The result is that the significance values for the targets on the microarray can maintain the same rank order. The confidence interval reduced by the median confidence interval is shown as $L_{95}$+median($\mu_i$-$L_{i,95}$) in FIG. 12, where $\mu_i$ is the estimated mean for target i, $L_{i,95}$ is its lower 95% confidence interval, and the median is taken over all targets.

Next, the probability value for the null hypothesis that this target actually has modal copy number is obtained as the cumulative probability above $L_{95}$+median($\mu_i$-$L_{i,95}$) in the normal distribution fitted to the plausibly modal targets.

If the initial mean ratio estimate for the target is less than one, indicating the possibility of a copy number less than modal, then the above process is modified by replacing lower confidence limits with upper confidence limits everywhere. The probability value for the null hypothesis that such a target actually has modal copy number is obtained as the cumulative probability below $U_{95}$-median($U_{i,95}$-$\mu_i$) in the normal distribution fitted to the plausibly modal targets, where $U_{95}$ and $U_{i,95}$ are the corresponding upper confidence limits. By repeating the process for every target, the probability estimate for each target to have non-modal copy number is calculated (282).

FIG. 12 is a graphical representation of the comparison of the target-mean to the distribution of modal targets analysis 228 illustrated with the help of a distribution graph 400. The distribution curve 402 represents a normal distribution fitted to the "plausibly modal" targets. These targets are initially defined as those spots with normalized ratio preferably in the range 0.65 to 1.35. A mean 404 is denoted by $\mu_p$.

Another distribution curve 406 represents a sampling distribution of an exemplary target, i.e., a normal distribution with a mean equal to an estimated target mean $\mu_t$ 408, and a standard deviation equal to the standard error of the estimated mean 408. Although this example assumes a gain in copy number, losses are represented in a similar fashion.

With 95% confidence, the probability that a given target is "plausibly modal" is no greater than the cumulative probability if the distribution curve 402 in the area to the right of $L_{95}$ (410). Since the probability limits thus computed will be overestimates in 95% of cases, better estimates may be obtained by reducing the per-target 95% confidence interval by the median confidence interval, while maintaining the rank order of the probability estimates. This is shown graphically by the line labeled $L_{95}$+median($\mu_i$-$_{i,95}$) in FIG. 12.

An alternative method is also based on a t-test formulation, which works with data internal to the analysis of a single chip (adapted difference of two means).

Normal copy number spots are found by a simple rule (lie between a lower and upper threshold; this could be replaced by a formal outlier analysis). These are then used to estimate the mean and variance for apparently normal spots. Then every target in turn is compared with this distribution, using a difference of means t-test. The null hypothesis is as follows: that the observed mean for the target, given its within-target variance, is not significantly different from the mean of the set of apparently normal spots given their estimated variance. This is different from the formulation of a standard difference of means t-test, because the reference population is believed not to have a homogeneous distribution, but rather is comprised of a distribution of per-target distributions. Thus the inter-target variance of the target being tested plays a different and more significant role than in the standard formulation. The adapted formula is as follows:

$$t=(M_T-M_P)/\text{sqrt}((V_T+V_P-\text{med}(V_i))/(1/N_T+1/N_P))$$
$$\text{degrees of freedom}=N_T+N_P-2,$$

where T indexes the target being tested, and $M_T$, $V_T$ and $N_T$ are its estimated mean and variance, and its number of spots respectively. $M_P$, $V_P$ and $N_P$ are the estimated mean and variance, and the number of spots, for the set of apparently normal spots. Med($V_i$) is the median of the per-target variances for the chip.

Compared with a standard test for equality of two means, this test gives extra weight to the tested target's variance, so that a target with higher CV will have a lower t-value than a low-CV target. In the standard formulation, because $N_T \ll N_P$, the tested target's variance is swamped by the weight applied to the variance of the apparently normal spots. The consequence is that the significance levels or p-values obtained from the computed t-value and the degrees of freedom must be interpreted with care. These p-values are indicative of relative significance.

As an example, the actual results of a DNA chip subject to the targets analysis process 228 is described below. Table A illustrates exemplary results for a genomic microarray of 190 targets each with three replicate spots:

TABLE A

| Name of target | Number of target spots | Ratio Mean | Ratio SD | Significance (P <) |
|---|---|---|---|---|
| FGR; SRC2 | 3 | 1.01 | 0.195 | |
| MYCN, N-myc | 3 | 0.95 | 0.004 | |
| PIK3CA | 3 | 1.04 | 0.075 | |
| EGFR; ERBB1 | 3 | 1.10 | 0.040 | |
| FGFR1, FLG | 3 | 1.10 | 0.098 | |
| FGFR2, BEK | 3 | 1.15 | 0.040 | |
| EMS1 | 3 | 1.12 | 0.030 | |
| CCND2 | 3 | 1.09 | 0.078 | |
| AR 3' | 3 | 0.78 | 0.009 | 0.005 |
| STK15; BTAK, | 3 | 1.02 | 0.019 | |
| ZNF217; ZABC1 | 3 | 0.93 | 0.004 | |
| AR 5' | 3 | 0.76 | 0.015 | 0.005 |
| 18p Tel 26806919 | 3 | 0.92 | 0.015 | |
| 9q Tel 26806923 | 3 | 1.02 | 0.007 | |
| SRY 26806944 | 3 | 1.55 | 0.014 | |
| D14S362 | 3 | 0.89 | 0.010 | |
| D2S2983 | 3 | 0.97 | 0.010 | |
| 4q Tel | 3 | 0.78 | 0.006 | 0.005 |
| STS NB268175V | 3 | 0.65 | 0.018 | 0.001 |
| TOP2B | 3 | 0.92 | 0.040 | |
| AKT3 NB268175Z | 3 | 0.89 | 0.043 | |
| PPARBP | 3 | 1.16 | 0.013 | |
| 3' KAL | 3 | 0.77 | 0.008 | 0.002 |
| XIST 26806956 | 2 | 0.81 | 0.005 | |

The number of replicate spots is usually 3, and a number of replicates which is fewer than 3 indicates a spot rejected because of debris or similar problem). The mean represents the value for the target of the normalized per-spot ratios. The standard deviation (SD) indicates values for the target of the normalized per-spot ratios, and the significance column shows the difference between the target's mean ratio and the mean modal ratio, expressed as the probability that the target is in fact a member of the modal distribution.

Each target covers approximately 100-200 kbp of the genome representing either a single gene (e.g., CCND2), a small number of contiguous genes (e.g., CSE1L+CAS), or a similar-sized genomic region not yet characterized (e.g., 3p Tel).

The chip is hybridized with normal human male DNA (test) and normal human female DNA (reference). Because males have one X chromosome while females have two, gene targets that lie on the X chromosome (e.g., AR3', AR5', XIST, KAL having 2 targets, STS having 2 targets) show a significantly reduced ratio. Similarly, the single target that lies on the Y chromosome (SRY) shows a significantly increased ratio. These targets are, e.g., AR 3' AR 5', 4q Tel, as shown in Table A above. All other targets lie on chromosomes 1 through 22 where both males and females have two copies, and thus show normalized ratios close to 1.0.

As illustrated in Table A, six of the seven X chromosome targets have ratios that are significantly lower (right-hand column) than the modal value, and are therefore true positives, while one (XIST) is not significant and is therefore a false negative. The ratio of SRY (Y chromosome) is significantly increased and this is also a true positive. 4q Tel also shows a significant ratio decrease, which provides the single false positive on this example microarray.

The relationships of the above described data can be understood in conjunction with Table B, which further describes the subset of the data described in Table A above:

TABLE B

| | Number of target spots | Ratio Mean | Ratio SD | Significance (P < . . . ) |
|---|---|---|---|---|
| Modal mean, SD | | 1.004 | 0.081 | |
| AR 3' | 3 | 0.78 | 0.009 | 0.005 |
| AR 5' | 3 | 0.76 | 0.015 | 0.005 |
| STS NB268175V | 3 | 0.65 | 0.018 | 0.001 |
| STS 26806942 | 3 | 0.67 | 0.010 | 0.001 |
| 3' KAL | 3 | 0.77 | 0.008 | 0.002 |
| KAL 26806972 | 3 | 0.69 | 0.005 | 0.001 |
| XIST 26806956 | 2 | 0.81 | 0.005 | |
| SRY 26806944 | 3 | 1.55 | 0.014 | 0.001 |
| 4q Tel 11 | 3 | 0.78 | 0.006 | 0.005 |

The modal mean and SD represent the mean and standard deviation of the normalized ratios of the subset of targets identified as "plausibly modal" by the target-modal statistical analysis 228. This is the baseline distribution with which every target mean ratio is compared individually to determine likelihood of being non-modal.

Subsequently, true-positive X chromosome targets are shown in the next six rows from AR 3' to KAL 26806972. The significance levels of their decreased mean ratios vary, depending both on the difference from the modal mean value 1.004, and the standard deviation of the target. For example, 3'KAL has both a lower mean ratio and a smaller standard deviation, and consequently a smaller confidence interval around the mean ratio than AR 3'. Therefore, it has higher significance (smaller p-value) for being non-modal.

Although AR5' has lower mean ratio than 3'KAL, it has a higher standard deviation and wider confidence interval. In computing the significance, the wider confidence interval dominates the mean ratio, with the result that the significance of the AR5' result is actually less than the significance for 3'KAL.

Next, data for XIST is shown having a false negative result. The low significance is caused by two factors, namely, the relatively high mean ratio of 0.81 having a small difference from the modal mean of 1.004 and (ii) the confidence interval being particularly wide because XIST is represented by only two spots.

Furthermore, the estimated standard deviation of an observed distribution may be converted to a confidence interval on the mean of the distribution by dividing by the square root of the number of samples and then multiplying by a suitable factor with this factor increasing rapidly as the number of samples decreases. Consequently, if the estimated standard deviations are equal, the confidence interval for a target with 2 spots becomes approximately 2.6 times wider than the confidence interval for a target with 3 spots.

After XIST, Table B shows data for SRY, a true positive target on the Y chromosome. Finally, Table B shows the data for 4q Tel, a target region at the tip of the long arm of chromosome 4. The low ratio for this target is unexpected and unexplained and is thus a false positive.

The experiment is expected to produce false positives with the numbers observed increasing with higher p-values, i.e., lower significance levels. In the case of 4q Tel, the p is less than 0.005. False positives with this significance level can be expected to occur at a frequency of approximately one in every 200 targets. The microarray analyzed in Tables A and B has 190 targets of which 182 are expected to have near-modal ratios. Therefore, one false positive at this significance level is not uncommon.

Other Embodiments

Although the example described above with reference to FIGS. 1-12 relates to single copy change detection processes, other fields of application are entirely within the scope of the invention, especially in the broad sector of microarray processes. Thus, a number of embodiments of the invention have been described. Nevertheless, it will be understood that various modifications may be made without departing from the spirit and scope of the invention. Furthermore, although the example describe above provides an analyzing process 110 having a particular order, the order of the various processes of the analyzing process 110 may be performed in any order or even in parallel as appropriate for obtaining a suitable image. Accordingly, other embodiments are within the scope of the following claims.

What is claimed is:

1. A method of detecting single copy number variation in a target spot of a genomic microarray comprising:
   acquiring an image of said microarray including said target spot;
   processing the image to correct for chip misalignment;
   processing the image to correct for background noise;
   analyzing the image to identify a target patch;
   analyzing the image to edit debris;
   analyzing the image to correct for ratio bias;
   detecting single copy number variation in the target spot by an objective statistical analysis;
   wherein the genomic microarray includes a test genomic material marked with receptors having a first wavelength and a reference genomic material marked with receptors having a second wavelength, the test and reference genomic materials forming the target spot by a hybridization process;
   further comprising measuring a fluorescent signal intensity of the target spot from the test genomic material and the reference genomic material, wherein the fluorescent signal intensity of the first wavelength is proportional to a copy number of the test genomic material and the fluorescent signal intensity of the second wavelength is proportional to a copy number of the reference genomic material;
   obtaining an image of a theoretical set of patches; and,
   cross-correlating the image of the theoretical set of patches to the image of the microarray.

2. The method of claim 1, wherein the target spot is Deoxyribonucleic Acid (DNA).

3. The method of claim 1, further comprising preparing a genomic material prior to acquiring the image and generating an array of the genomic material on a solid substrate.

4. The method of claim 1, wherein the genomic material includes a range between 50 and 200 kbp.

5. The method of claim 3, wherein preparing the genomic material includes isolating the genomic material by an extraction process followed by nick translation labeling and polymerase chain reaction (PCR) labeling.

6. The method of claim 1, wherein the hybridization process is a comparative genomic hybridization (CGH) process.

7. The method of claim 1, wherein subsequent to acquiring the image of the genomic microarray and prior to correcting for the background noise, processing the image includes automatically detecting misalignment of the genomic microarray and correcting for rotation of the genomic microarray.

8. A method of detecting single copy number variation in a target spot of a genomic microarray comprising:
   acquiring an image of said microarray including said target spot;
   processing the image to correct for chip misalignment;
   processing the image to correct for background noise;
   analyzing the image to identify a target patch;
   analyzing the image to edit debris;
   analyzing the image to correct for ratio bias;
   detecting single copy number variation in the target spot by an objective statistical analysis;
   wherein the genomic microarray includes a test genomic material marked with receptors having a first wavelength and a reference genomic material marked with receptors having a second wavelength, the test and reference genomic materials forming the target spot by a hybridization process;
   further comprising measuring a fluorescent signal intensity of the target spot from the test genomic material and the reference genomic material, wherein the fluorescent signal intensity of the first wavelength is proportional to a copy number of the test genomic material and the fluorescent signal intensity of the second wavelength is proportional to a copy number of the reference genomic material;
wherein correcting of the background noise includes:
   computing the acquired image;
   computing a minimum image based on the computed acquired image;
   computing a maximum image based on the computed minimum image;
   subtracting a background image from the computed acquired image to obtain a resulting image; and,
   optimizing the correction for the background noise by identifying a background peak of the resulting image and subtracting the resulting image to obtain a mean value of zero for a corrected image.

9. The method of claim 8, wherein the corrected image includes pixels having signed values.

10. The method of claim 8, wherein identifying a target patch includes:
   obtaining an image of a theoretical set of patches; and,
   cross-correlating the image of the theoretical set of patches to the image of the microarray.

11. The method of claim 9, wherein following identifying a target patch, the method further comprises:
   computing a threshold by analyzing a pixel intensity of the counterstained image to determine an initial segmentation of the target spot; and,
   performing a process for spot shape analysis and spot segmentation.

12. The method of claim 11, further comprising:
   performing a spot identification analysis; and
   performing an artifact spot exclusion process wherein an artifact spot is automatically excluded.

13. The method of claim 1, wherein editing of debris includes automatically removing spot debris by recognizing and excluding spot pixels within a target spot having outlying intensity relative to a majority of the spot pixels.

14. The method of claim 13, wherein editing of debris includes:
   transforming test and reference intensities to polar coordinates having as a first coordinate the overall intensity of spot signals and having as a second coordinate the ratio;
   applying a standard statistical test for outliers to the first and second coordinates; and,
   analyzing the shape of excluded spot pixels.

15. A method of detecting single copy number variation in a target spot of a genomic microarray comprising:
   acquiring an image of said microarray including said target spot;
   processing the image to correct for chip misalignment;
   processing the image to correct for background noise;
   analyzing the image to identify a target patch;
   analyzing the image to edit debris;
   analyzing the image to correct for ratio bias;
   detecting single copy number variation in the target spot by an objective statistical analysis;
   wherein the genomic microarray includes a test genomic material marked with receptors having a first wavelength and a reference genomic material marked with receptors having a second wavelength, the test and reference genomic materials forming the target spot by a hybridization process;
   further comprising a fluorescent signal intensity of the target spot from the test genomic material and the reference genomic material, wherein the fluorescent signal intensity of the first wavelength is proportional to a copy number of the test genomic material and the fluorescent signal intensity of the second wavelength is proportional to a copy number of the reference genomic material;
   further comprising:
   computing a ratio based on a test and a reference fluorescence signal intensity value associated with the target spot;
   further wherein correcting for ratio bias includes measuring a raw ratio representing a ratio of total test fluorescence intensity from the target spot and a total reference fluorescence intensity from the target spot;
   normalizing the raw ratio by dividing the raw ratio of each spot by the median over all spots of the raw ratio; and
   further wherein correcting for ratio bias includes:
   selecting a subset of spots that have a normalized observed ratio approximately equal to 1.0, referred to as "plausibly modal spots";
   modeling an effect of bias in said subset of plausibly modal spots by the equation $R = r^{-B}$, where R represents said normalized observed ratio, r is the reference intensity of the spot, and B is a bias parameter that is constant across all spots of a microarray;
   estimating the optimum value of B from said subset of plausibly modal spots;
   performing ratio bias correction of unknown data by applying the correction formula $R_{corrected} = R_{original} / R_{predicted}$ and choosing a value of B that minimizes the mean square difference between the set of normalized original ratios, and the set of normalized predicted ratios according to equation $R=r^{-B}$.

16. A method of detecting single copy number variation in a target spot of a genomic microarray comprising:
    acquiring an image of said microarray including said target spot;
    processing the image to correct for chip misalignment;
    processing the image to correct for background noise;
    analyzing to identify a target patch;
    analyzing the image to edit debris;
    analyzing the image to correct for ratio bias;
    detecting single copy number variation in the target spot by an objective statistical analysis;
    wherein the genomic microarray includes a test genomic material marked with receptors having a first wavelength and a reference receptors having a second wavelength, the test and reference genomic materials forming the target spot by a hybridization process;
    further comprising measuring a fluorescent signal intensity of the target spot from the test genomic material and the reference genomic material, wherein the fluorescent signal intensity of the first wavelength is proportional to a copy number of the test genomic material and the fluorescent signal intensity of the second wavelength is proportional to a copy number of the reference genomic material;
    wherein the objective statistical analysis includes a target-modal statistical analysis; and
    wherein the target-modal statistical analysis includes:
    for a selected subset of plausibly modal targets, estimating a statistical distribution of ratios of plausibly modal targets; and
    for each target of the microarray, computing an estimated target mean and a lower 95% confidence interval limit; and
    for each target, reducing the lower 95% confidence interval limit by the median 95% confidence interval over all targets of the microarray; and
    for each target, calculating a confidence estimate.

17. The method of claim 16, further comprising estimating a relative copy number of a genomic sequence from the target spot by the target-modal statistical analysis.

18. A computer program product residing on a computer storage medium having instructions stored thereon which, when executed by a logic processor, cause the processor to:
    acquire an image of a microarray including a target spot;
    process the image to correct for background noise and chip misalignment;
    analyze the image to detect target spots;
    analyze the image to identify the target patch, edit debris, and correct for ratio bias;
    detect single copy number variation in the target spot by an objective statistical analysis;
    wherein genomic microarray includes a test genomic material marked with receptors having a first wavelength and a reference genomic material marked with receptors having a second wavelength, the test and reference genomic materials forming the target spot by a hybridization process;
    measure a fluorescent signal intensity of the target spot from the test genomic material and the reference genomic material, wherein the fluorescent signal intensity of the first wavelength is proportional to a copy number of the test genomic material and the fluorescent signal intensity of the second wavelength is proportional to a copy number of the reference genomic material;
    obtain an image of a theoretical set of patches; and
    cross-correlate the image of the theoretical set of patches to the image of the microarray.

19. The computer program product of claim 18, wherein the target spot is Deoxyribonucleic Acid (DNA).

20. The computer program product of claim 18, wherein subsequent to causing the processor to acquire the image of the genomic microarray and prior to causing the processor to process the image for correcting the background noise, causing the processor to process the image further includes automatically causing the processor to detect misalignment of the genomic microarray and correct rotation of the genomic microarray.

21. The computer program product of claim 18, wherein the genomic material includes a range between 50 kbp and 200 kbp.

22. The computer program product of claim 18, wherein the genomic microarray includes a test genomic material marked with a first label having a first wavelength and a reference genomic material marked with a second label having a second wavelength, both test and reference genomic materials forming the target spot by a hybridization process.

23. The computer program product of claim 18, further causing the processor to:
    compute a ratio based on a test and a reference fluorescence signal intensity value associated with the target spot.

24. The computer program product of claim 20, wherein correcting for ratio bias includes measuring a raw ratio representing a ratio of total test fluorescence intensity from the test fluorescence signal intensity value and a total reference fluorescence intensity from the reference fluorescence signal intensity value.

25. The computer program product of claim 24, further causing the processor to normalize the raw ratio by mathematical computation.

26. The computer program product of claim 25, wherein correcting for ratio bias includes:
    selecting a subset of spots that have a normalized observed ratio approximately equal to 1.0, referred to as "plausibly modal spots";
    modeling an effect of bias in said subset of plausibly modal spots by the equation $R=r^{-B}$, where R represents said normalized observed ratio, r is the reference intensity of the spot, and B is a bias parameter that is constant across all spots of a microarray;
    estimating the optimum value of B from said subset of plausibly modal spots;
    performing ratio bias correction of unknown data by applying the correction formula $R_{corrected}=R_{original}/R_{predicted}$ and choosing a value of B that minimizes the mean square difference between the set of normalized original ratios, and the set of normalized predicted ratios according to equation $R=r^{-B}$.

27. The computer program product of claim 18, wherein the objective statistical analysis includes a target-modal statistical analysis.

28. The computer program product of claim 27, wherein the target-modal statistical analysis includes:
    for a selected subset of plausibly modal targets, estimating a statistical distribution of ratios of plausibly modal targets; and
    for each target of the microarray, computing an estimated target mean and a lower 95% confidence interval limit; and
    for each target, modifying the lower 95% confidence interval limit by the median 95% confidence interval over all targets of the microarray; and for each target, calculating a confidence estimate for the target by comparing the adjusted confidence interval limit with the distribution of ratios of plausibly modal targets.

29. A processor and a memory configured to:
acquire an image of a microarray including at least one target spot;
process the image to correct for background noise and chip misalignment;
analyze the image to detect target spots;
analyze the image to identify a target patch, edit debris, and correct for ratio bias; and,
detect single copy number variation in a target spot by an objective statistical analysis;
wherein the microarray includes a test genomic material marked with receptors having a first wavelength and a reference genomic material marked with receptors having a second wavelength, the test and reference genomic materials forming the target spot by a hybridization process;
measure a fluorescent signal intensity of the target spot from the test genomic material and the reference genomic material, wherein the fluorescent signal intensity of the first wavelength is proportional to a copy number of the test genomic material and the fluorescent signal intensity of the second wavelength is proportional to a copy number of the reference genomic material;
obtain an image of a theoretical set of patches; and,
cross-correlate the image of the theoretical set of patches to the image of the microarray.

30. A system comprising:
means for acquiring an image of a microarray including at least one target spot;
means for processing the image to correct for background noise and chip misalignment;
means to analyze the image to detect target spots;
means for analyzing the image to identify a target patch, edit debris, and correct for ratio bias; and,
means for detecting single copy number variation in the target spot by an objective statistical analysis;
wherein the microarray includes a test genomic material marked with receptors having a first wavelength and a reference genomic material marked with receptors having a second wavelength, the test and reference genomic materials forming the target spot by a hybridization process;
means for measuring a fluorescent signal intensity of the target spot from the test genomic material and the reference genomic material, wherein the fluorescent signal intensity of the first wavelength is proportional to a copy number of the test genomic material and the fluorescent signal intensity of the second wavelength is proportional to a copy number of the reference genomic material;
means for obtaining an image of a theoretical set of patches; and,
means for cross-correlating the image of the theoretical set of patches to the image of the microarray.

* * * * *

UNITED STATES PATENT AND TRADEMARK OFFICE
CERTIFICATE OF CORRECTION

PATENT NO. : 7,636,636 B2
APPLICATION NO. : 10/269723
DATED : December 22, 2009
INVENTOR(S) : James R. Piper Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 361 days.

Signed and Sealed this

Twenty-first Day of December, 2010

David J. Kappos
*Director of the United States Patent and Trademark Office*